United States Patent [19]

Amick et al.

[11] Patent Number: 5,118,681

[45] Date of Patent: Jun. 2, 1992

[54] S-BETA-DICARBONYL SUBSTITUTED BETA-THIOACRYLAMIDE BIOCIDES AND FUNGICIDES

[75] Inventors: David R. Amick, Doylestown; Katherine E. Flynn, Lansdale; Cherylann Schieber, Narberth, all of Pa.

[73] Assignee: Rohm and Haas Company, Philadelphia, Pa.

[21] Appl. No.: 387,053

[22] Filed: Jul. 28, 1989

[51] Int. Cl.$^5$ .................. A61K 31/16; A61K 31/165; A61K 31/38; A61K 31/505

[52] U.S. Cl. .................. 514/238.8; 514/272; 514/371; 514/428; 514/447; 514/352; 514/370; 514/372; 514/549; 514/616; 514/627; 544/158; 544/332; 544/159; 546/309; 560/44; 560/47; 560/15; 564/153; 564/154; 564/199

[58] Field of Search .................. 560/44, 47, 15; 564/153, 154, 199; 514/352, 370, 372, 549, 616, 627, 238.8, 272, 371, 428, 447; 546/309; 548/195, 571; 549/72

[56] References Cited

U.S. PATENT DOCUMENTS 3,914,301 10/1975 Miller et al. .................. 514/627

OTHER PUBLICATIONS

W. D. Crow and I. Gosney, Aust J. Chem, 22, 765–774 (1969).
W. D. Crow and I. Gosney, Tetrahedron, 26, 1463–1473 (1970).

*Primary Examiner*—Mukund J. Shah
*Assistant Examiner*—E. C. Ward
*Attorney, Agent, or Firm*—Michael B. Fein

[57] ABSTRACT

S-beta-dicarbonyl substituted beta-thioacrylamide compounds have been discovered to be useful as biocides and fungicides. Compositions comprising the compound and isothiazolin-3-ones and/or carries. methods of preparation of the compounds and methods of using the compounds and compositions are also disclosed.

14 Claims, No Drawings

S-BETA-DICARBONYL SUBSTITUTED BETA-THIOACRYLAMIDE BIOCIDES AND FUNGICIDES

BACKGROUND OF THE INVENTION

1. Field of the Invention

This invention relates to biocides and fungicides.

2. Description of the Prior Art

The following references were considered pertinent, but do not describe or suggest the present invention: Miller, et al., U.S. Pat. No. 3,914,301 (Oct. 21, 1975), commonly assigned, and W. D. Crow and I. Gosney, Aust. J. Chem., 22, 765-774 (1969).

3. Summary of the Invention

There is a need for alternative biocides and fungicides, especially improved ones.

It is therefore an object of the present invention to provide novel compounds which are useful in any locus subject to contamination by bacteria or fungi.

These objects and others as will become apparent from the following detailed description, are achieved by the present invention which in one aspect comprises a compound of the formula

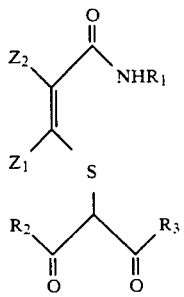

wherein $R_1$ is ($C_5$-$C_{10}$)alkyl or ($C_5$-$C_7$) cycloalkyl; $R_2$ and $R_3$ are independently selected organic radicals which, when taken together, can form a cyclic structure; and $Z_1$ and $Z_2$ are independently selected from hydrogen, halogen and ($C_1$-$C_4$) alkyl.

In another aspect the invention comprises the use of such a compound as a biocide or as a fungicide, and compositions comprising such compounds in fungicidally effective amount in an agronomically acceptably carrier. In another aspect the invention comprises a method of controlling or inhibiting growth of bacteria in a locus comprising incorporating into or onto the locus a biocidally effective amount of the compound.

DETAILED DESCRIPTION OF THE INVENTION AND THE PREFERRED EMBODIMENTS

The novel compounds of the invention have been found to be useful as bactericides or as fungicides or both. The compounds of the invention have the formula

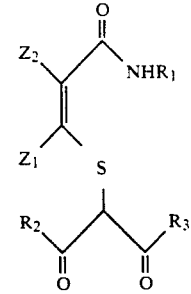

wherein $R_1$ is ($C_5$-$C_{10}$) alkyl or ($C_5$-$C_7$) cycloalkyl; $R_2$ and $R_3$ are independently selected organic radicals which, when taken together, can form a cyclic structure; and $Z_1$ and $Z_2$ are independently selected from hydrogen, halogen and ($C_1$-$C_4$) alkyl.

It is preferred that $R_2$ is EtO— and $R_3$ is selected from

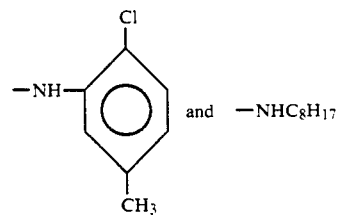

It is especially preferred where $R_2$ is —$CH_3$ and $R_3$ is —$CH_3$.

Preferably $Z_1$ and $Z_2$ are H or Cl, most preferably hydrogen. $R_1$ is preferably -n-$C_8H_{17}$.

In another preferred embodiment, $R_1$ and $R_2$ are independently selected from the group consisting of unsubstituted and substituted alkoxy, alkyl, amino, alkyl amino, arylamine, aralkylamino, alkarylamino, heterocyclic substituted amino and alkylamino, N-containing heterocycles, aryl, and alkenyl groups.

The beta-thioacrylamides of the invention can be used in any locus subject to contamination by bacteria or fungi. Typical loci subject to contamination by bacteria are in aqueous systems such as water cooling, laundry wash water, oil/water systems such as cutting oils, oil fields and the like where microorganisms need to be killed or where their growth needs to be controlled.

Specific loci for bacteriostatic and fungistatic application include disinfectants, sanitizers, cleaners, deodorizers, liquid and powder soaps, skin removers, oil and grease removers, food processing chemicals, dairy chemicals, food preservatives, animal food preservatives, wood preservation, paint, lazures, stains, mildewcides, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, jet fuel, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes, electrodepositions systems, diagnostic products, medical devices, water purification systems, filtration systems, fishnets, mariene antifoulants and other applications where water and organic materials come in contact under conditions which allow the growth of undesired microorganisms. Solutions of beta-thioacrylamides can also applied to a solid substrate, such as fabric, leather, or wood, as a preservative, or admixed with plastics. It is known in the art that the performance of biocides can frequently be enhanced by combination with one or more other biocides. In fact, there have been numerous examples of synergistic combinations of biocides. Thus, other known biocides may be combined advantageously with the beta-thioacrylamides of this invention. See Industrial Antimicrobial Agents Encyclopedia of Chemical Technolgy, Volume 13, for a list of suitable other biocides. More specific industries and applications for the compounds are:

| Industry | Application |
| --- | --- |
| Adhesives, Sealants | Adhesives |
|  | Caulks |
|  | sealants |
| agriculture/food chain | adjuvant preservation |
|  | agricultural active ingredient |
|  | agricultural chemical preservative |
|  | agricultural formulations preservation |
|  | animal feed preservation |
|  | dairy chemicals |
|  | fertilizer preservation |
|  | food preservation |
|  | food processing chemicals |
|  | grain preservation |
|  | post-harvest produce protection |
|  | sugar processing |
|  | tobacco |
| Construction products | asphalt/concrete |
|  | cement modifiers |
|  | construction products |
|  | roof mastics |
|  | synthetic stucco |
|  | wall mastics |
|  | joint cement |
| Cosmetics and toiletries | Cosmetics |
|  | raw materials for cosmetics, toiletries |
|  | toiletries |
| Disinfectants, antiseptics | antiseptic |
|  | disinfectant |
| Emulsions, dispersions | aqueous dispersions |
|  | dispersed pigments |
|  | latex |
|  | photographic emulsions |
|  | pigment slurries |
|  | polymer latices |
| formulated household products | fabric softeners |
|  | polishes |
|  | waxes |
|  | hand dish detergents |
|  | raw materials |
|  | liquid detergents |
|  | hand soaps |
| Industrial processing, misc | electrodeposition paint, baths, rinses, |
|  | electrodeposition pre-treatment, post rinses |
|  | Industrial fluids preservation |
|  | pasteurization baths |
|  | process aid preservation |
| Industrial water treatment | air washers |
|  | cooling towers |
|  | cooling water |
|  | water cooling |
|  | preservation/treatment of wooden cooling tower slats and structural members |
|  | can warmers |
|  | brewery pasteurization |
|  | closed loop water cooling systems |
| Laundry | household laundry products |
|  | laundered goods |
|  | laundry wash water |
|  | sanitizers-laundry |

-continued

| Industry | Application |
| --- | --- |
| Leather, Leather products | leather and hide |
|  | leather and hide products |
| Lubricants, hydraulic aids | automotive lubricants and fluids |
|  | conveyor lubricants |
|  | greases |
|  | hydraulic fluids |
|  | lubricants |
| Medical devices | diagnostic enzymes |
|  | diagnostic kits |
|  | medical devices |
| metalworking & related app's | cutting fluids |
|  | Metal cleaning |
|  | metalworking fluids |
| Odor control (active ingredient) | air conditioning |
|  | animal bedding |
|  | cat litter |
|  | chemical toilet prep'ns |
|  | deodorizers |
|  | humidifiers |
|  | industrial deodorants |
|  | sanitary formulations |
|  | toilet bowls |
| Paints and coatings coating | emulsions |
|  | paints |
| Paper and wood pulp, their products | absorbant materials of paper and wood pulp |
|  | packaging materials of paper and wood pulp |
|  | paper |
|  | paper products |
|  | paper treatment |
|  | soap wrap |
|  | wood pulp |
|  | wood pulp products |
| paper mill | paper mill slimicides |
|  | pulp and paper slurries |
| Petroleum refining, fuels | aviation fuels (jet fuel, aviation gas) |
|  | crude oils |
|  | burner, diesel and turbine fuel oils |
|  | coal slurries |
|  | diesel fuel additives |
|  | diesel fuels |
|  | fuels |
|  | gasoline |
|  | heating oils |
|  | hydrocarbons |
|  | Kerosene |
|  | liquefied petroleum gas |
|  | petrochemical feedstocks |
|  | petroleum products, storage, transportation and production |
|  | recycled petroleum products |
|  | residual fuel oils |
|  | turbine oils |
| Photographic Chemicals and process | Photographic processing - wash water, rinses |
|  | photoprocessing |
|  | Photoplate processing chemicals (developers, stabilizers etc) |
| Printing | Fountain solutions (printing) |
|  | Ink components (pigments, resins, solvents, etc) |
|  | Inks |
| sanitizers (active) | sanitizers |
|  | sanitizers-dairy |
|  | sanitizers-dental |
|  | sanitizers-fermentation |
|  | sanitizers-food preparation |
|  | sanitizers-food processing |
|  | sanitizers-medical |
|  | sanitizers-rendering |
|  | sanitizers-veterinary |
| Soaps, detergents, cleaners | cleaners |
|  | detergents |
|  | household cleaners |
|  | industrial cleaners |
|  | liquid soaps |
|  | oil and grease remover |
|  | powdered soaps |
|  | raw materials for cleaning products |
|  | soaps |

| Industry | Application |
|---|---|
| Textiles, textile products | surfactants<br>bonded fabrics<br>burlap<br>canvas<br>canvas goods<br>carpet backing<br>carpets<br>clothing<br>coated fabrics<br>curtains<br>draperies<br>engineering textiles<br>fibers<br>geotextiles<br>goods made of textiles<br>knitted fabrics<br>nets<br>nonwoven fabrics<br>rope<br>rugs<br>textile accessories<br>textile products<br>textiles<br>upholstery<br>woven fabrics<br>yarn |
| Textile processing | dye fixatives<br>dyes<br>fiber lubricants<br>hand modifiers<br>sizes<br>Textile processing fluids |
| Therapeutic (active or preservative) | animal health/veterinary<br>aquaculture<br>dental<br>human health<br>pharmaceutical/therapeutic |
| water purification | charcoal beds<br>deionization resins<br>filters<br>membranes<br>reverse osmosis membranes<br>ultrafilters<br>Water purification<br>water purification pipes, tubing |
| wood applications | lazures (wood stains)<br>wood<br>wood products |
| Miscellaneous | alcohols<br>bedding incorporating water or gels<br>ceramic<br>contact lens cases-leaching<br>electronic circuitry<br>electronics chemicals<br>enzymes-food production<br>enzymes<br>enzymes-industrial<br>gel cushions<br>marine antifoulants<br>mildewcides<br>wood<br>plastics<br>laundry<br>mining<br>natural rubber latex<br>oil field injection waters including enhanced recover injection fluids, drilling, fracturing and completion fluids<br>pipes<br>plastics<br>polymer systems<br>polymers and resins (synthetic and natural)<br>reagent preservation<br>rubber<br>rubber products<br>skin remover<br>solid protective/decorative films<br>stains<br>swimming pools |

| Industry | Application |
|---|---|
| | waste treatment<br>water beds |

The beta-thioacrylamides compounds of the invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, but the effective amount for application is usually from about 5 grams (gm) to about 22 kilograms (kg), preferably from about 0.010 to about 1.0 kg per hectare.

As a seed protectant, the amount of fungicide coated on the seed is usually at a dosage rate of about 0.0001 to about 10 grams (gm) and preferably from about 0.1 to about 10 gm per 1 kilogram of seed. As a soil fungicide the beta-thioacrylamides can be incorporated in the soil or applied to the surface usually at a rate of 0.01 to about 22 kg, preferably about 0.05 to about 11 kg and more preferably from about 0.1 to about 3.3 kg per hectare. As a foliar fungicide the beta-thioacrylamides can be applied at a rate of from about 0.01 to about 11 kg, preferably from about 0.02 to about 5.5 kg and more preferably from about 0.1 to about 3.3 kg per hectare.

The present invention is useful for the control of fungi and can be utilized at various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these beta-thioacrylamides can be formulated as wettable powders, emulsifiable concentrates, dusts, granular formulations, aerosols, or flowable emulsion concentrates. In such formulations, the beta-thioacrylamides are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers and Detergents, McCutcheon's Emulsifiers and Detergents/Functional Materials and McCutcheon's Functional Materials* all published annually by McCutcheon Division of MC Publishing Company (New Jersey). In general, the beta-thioacrylamides of this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50% (weight percentage). For the preparation of emulsifiable concentrates, the beta-thioacrylamides can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75% (weight percent). Water based flowable formulations of the beta-thioacrylamides can be prepared with a concentration of active ingredients in the range of 5 to 70% by weight, preferably 20 to 50% by weight.

A typical flowable formulation is prepared by wet-milling a mixture of 35 parts of beta-thioacrylamides, 10 parts of Barden clay, 4 parts of sodium lignosulfonate, 1 part of an anionic wetting agent and 50 parts of water.

Wettable powders suitable for spraying can be prepared by admixing the beta-thioacrylamide compound with a finely divided solid, such as clays, inorganic silicates and carbonates, and silicas and incorporating wetting agents, sticking agents, and/or dispersing agents in such mixtures. The concentration of active ingredients in such formulations is usually in the range of 5% to 98%, preferably 40% to 75% (weight percent) obtained by blending 50 parts of an active ingredient selected from the S-beta-dicarbonyl substituted beta-thioacrylamides of Examples 1-69, 45 parts of a synthetic precipitated hydrated silicon dioxide sold under the trademark Hi-Sil, 1 part of an anionic naphthalenic sulfonate wetting agent and 4 parts of sodium lignosulfonate (Marasperse N-22). In another preparation of a kaolin type (Barden) clay is used in place of the Hi-Sil in the above wettable powder and in another such preparation 25% of the Hi-Sil is replaced with a synthetic sodium silico aluminate sold under the trademark Zeolex 7. Dusts are prepared by mixing the amides and salts and complexes thereof with finely divided inert solids which can be organic or inorganic in nature. Materials useful for this purpose include botanical flours, silicas, silicates, carbonates, talc and clays. One convenient method of preparing a dust is to dilute a wettable powder with a finely divided carrier. Dust concentrates containing 20% to 80% (weight percent) of the active ingredient are commonly made and are subsequently diluted to 1% to 10% use concentration.

The compounds of the present invention may also be utilized in combination with other fungicides such as:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate;

(c) heterocyclic structures such as: Systhane (a registered trademark of Rohm and Haas for myclobutanil), triademifon, N-trichloromethylthiotetrahydrophthalimide (captan), N-trichloromethylthiophthalimide (folpet), 2-heptadecyl-2-imidazole acetate (glyodine), 2-octylisothiazolone-3, 2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), methyl 1-(butylcarbamoyl)-2-benzimidazole carbamate (benomyl), 2,4'-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinclozolin), 3-(3,5-dichlorophenyl)-N-(1-methylethyl)-2,4-di-alpha-oxo-1-imidazolinecarboxamide (dichlorophenyl)-1,2-dimethylcyclopropane-1,2-dicarboximide (procymidone), beta-(4-chlorophenoxy)-alpha-(1,1-dimethylethyl)-1H-1,2,4-triazole-1-ethanol (triadimenol), 1-(4-chlorophenoxy)-3,3-dimethyl-1-(1H-1,2,4-triazol-1-yl)-2-butanone (triadimefon), beta-[(1,1'-biphenyl)-4-yloxy]-alpha-(1,1-dimethylethyl)-1H-1,2,4-triazole-1-ethanol (bitertanol), 2,3-dichloro-N-(4-fluorophenyl)maleimide (fluoroimide), 1-[2-(2,4-dichlorophenyl)-4-propyl-1,3-dioxolan-2-yl-methyl]-1H-1,2,4-triazole, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, alpha-(phenyl)-alpha-(2,14-dichlorophenyl)-5-pyrimidinyl-methanol (triarimol), cis-N-[1,1,2,2-tetrachloroethyl)-thio]-4-cyclohexene-1,2-dicarboximide, 3-[2-(3,5 -dimethyl-2-oxycyclohexyl)-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclodecyl-2,6-dimethyl-morpholine (dodemorph), and 6-methyl-2-oxo-1,3-dithiolo[4,5-b]-quinoxaline (quinomethionate);

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chlorneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sultone, dodecylguanidine acetate (dodine), phenylmercuric acetate, N-ethyl-mercuri-1,2,3,6-tetrahydro-3,6-endomethano-3,4,5,6,7,7-hexachlorophthalimide, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, 1,2-bis(3-methoxycarbonyl-2-thioureido) benzene (thiophanate-methyl).

The S-beta-dicarbonyl substituted beta-thioacrylamides of the present invention can be prepared by reacting an unsubstituted or substituted 4-isothiazolin-3-one with a suitable nucleophilic reagent. This reaction can be schematically represented as follows:

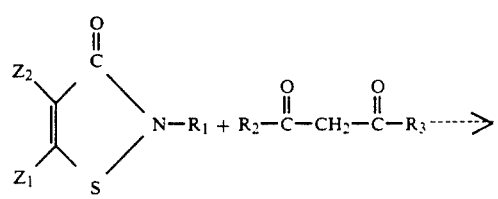

-continued

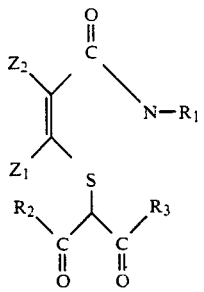

wherein $R_1$ is $(C_5-C_{10})$alkyl or $(C_5-C_7)$cycloalkyl; $R_2$ and $R_3$ are independently selected organic radicals which, when taken together, can form a cyclic structure; and $Z_1$ and $Z_2$ are independently selected from hydrogen, halogen, and $(C_1-C_4)$alkyl. Preferably, $R_2$ and $R_3$ are independently selected from the group consisting of unsubstituted and substituted alkoxy, alkyl, amino, alkylamino, arylamino, aralkylamino, alkarylamino, heterocyclic substituted amino and alkylamino, N-containing heterocycles, aryl, and alkenyl groups. Thus, some preferred, but not limiting, nucleophiles which can be used to cleave the 4-isothiazolin-3-one ring include compounds such as beta-diketones, beta-ketoesters, N-substituted acetoacetamides, acetoacetanilides, N-substituted malonamide esters, and N,N'-substituted malonamides.

In preparing the compounds of the invention, equimolar amounts of the 4-isothiazolin-3-one and the nucleophilic reagent are generally used. The convenient in-situ formation of sodium ethoxide from sodium metal in absolute ethanol can be advantageously used to facilitate the reaction between the 4-isothiazolin-3-one and the nucleophilic reagent by allowing the abstraction of a proton from the $R_2$—CO—$CH_2$—CO—$R_3$ nucleophilic reagent to take place. Alternative means for proton abstraction which are well known to those skilled in the art include, but are not limited to, the utilization of sodium hydride, lithium diisopropylamide which is conveniently made in situ from diisopropyl amine and n-butyllithium, and tetra-n-butylammonium fluoride. The reaction between the nucleophilic reagent and the 4-isothiazolin-3-one is generally carried out at a temperature of about $-10°$ C. to about $100°$ C., and preferably between $0°-25°$ C. in that range. Various organic solvents can be used in carrying out the reaction, if desired, with alcoholic solvents, acyclic or cyclic ethers, alkanes, or dialkyl amides being preferred. However, any solvent or mixture of solvents which will not interfere with the reaction can be used.

Under high pH conditions this reaction is reversable, resulting in compositions comprising both the compounds and the 4-isothiazolin-3-one precurser.

All of the 4-isothiazolin-3-one intermediates can be prepared by the cyclization of a substituted disulfidediamide having the formula:

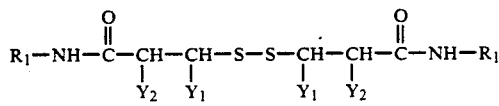

wherein $Y_1$ and $Y_2$ are hydrogen or $(C_1-C_4)$alkyl groups and $R_1$ is defined as above. The cyclization is accomplished by reacting the disulfidediamide with a halogenating agent. Any halogenating agent can be employed in this reaction, with chlorine and sulfuryl chloride being preferred. Cyclization of the disulfidediamide will take place when 3 mole equivalents of halogenating agent/mole equivalent of disulfidediamide are employed in the reaction. By providing an excess of halogenating agent, the 4-isothiazolin-3-one may be halogenated at the 4- and/or 5-positions of the ring. Where 5 mole equivalents of halogenating agent are available, mono-halogenation can take place. For dihalogenation, 7 mole equivalents of halogenating agent are required. The cyclization process will proceed over a broad temperature range and temperature is not critical to the reaction. Generally, the cyclization will be carried out in the range of $-10°$ C. to $100°$ C. The reaction is carried out in an inert non-aqueous solvent, such as ethyl acetate, ethylene dichloride, benzene, toluene, xylene or the like.

The following examples will further illustrate this invention, but are not intended to limit it in any way. All parts and percentages are by weight and all temperatures in degrees Centigrade, unless otherwise stated.

EXAMPLE 1

Preparation of N-n-Octyl-cis-3-[3-(2,4-pentanedionyl)thio]acrylamide

To a stirred solution of 2.41 mL (0.0235 mol) of 2,4-pentanedione in 20 mL of absolute ethanol was under nitrogen was added 8.78 mL (0.0235 mol) of a 21 wt % solution of sodium ethoxide in absolute ethanol. After 20 min a pale yellow slurry formed. This mixture was cooled to 0° C. and a solution of 5 g (0.0235 mol) of 2-n-octyl-4-isothiazolin-3-one in 5 mL of absolute ethanol was added dropwise. After the addition the mixture was allowed to warm to room temperature and to stir for 5 h. The mixture was then poured into 200 mL of 10% aqueous hydrochloric acid and extracted three times with ethyl acetate. The combined organic layers were washed once with water and several times with a saturated aqueous solution of sodium bicarbonate until the washes were neutral in pH. The organic layer was then washed with brine, dried over magnesium sulfate, and filtered. Removal of solvents gave a light yellow solid which was recrystallized from hexane/ethyl acetate to afford 4.84 g (66% yield) of N-n-octyl-cis-[3-(2,4-pentanedionyl)thio]acrylamide as a white crystalline solid, m.p. 87°–89° C.

EXAMPLE 2-7

Preparation of Other Compounds of the Invention

Example 1 was repeated with the replacement of the 2-n-octyl-4- isothiazolin-3-one by 2-n-octyl-4,5-dichloro-4-isothiazolin-3-one, 2-n-pentyl-4-isothiazolin-3-one, 2-n-heptyl-4-isothiazolin-3-one, 2-n-hexyl-4-isothiazolin-3-one, 2-cyclohexyl-4,5-dichloro-4-isothiazolin-3-one, and 2-n-hexyl-4,5-dichloro-4-isothiazolin-3-one to obtain Examples 2, 3, 4, 5, 6, and 7, respectively, as shown in Table 1. The preparation of these isothiazolone-3-one intermediates is described as follows:

A. Preparation of the 2-n-Octyl-4,5-dichloro-4-isothiazolin-3-one Intermediate for Example 2

In a four-necked, 3-liter flask equipped with a mechanical stirrer, a thermometer, a chlorine inlet, and a condenser connected to an acid scrubber was suspended 432.0 g (1.0 mol) of N,N'-di-n-octyl-3,3'-dithiodipropionamide in 930 ml of ethyl acetate. The suspension was heated to 60° C. and a total of 490 g (6.9 mol) of chlorine was introduced beneath the surface at a constant flow rate for 3 hours. During the first hour of the chlorine addition, the reaction was mildly exothermic and the temperature was maintained at 60° C. by external cooling. After the initial mild exotherm, the temperature started falling and external heating was required to hold the temperature at 60° C. After the chlorine addition, the solvent was removed under reduced pressure to give 590 g of amber colored, viscous liquid. The crude product was dissolved in 500 ml of hexane with stirring and cooled to 0° C. The solid which separated was removed by filtration and dried to give about 310 g (55% yield) of the 2-n-octyl-4,5-dichloro-4-isothiazolin-3-one intermediate, mp=44°-47° C.

B. Preparation of 2-n-Penyl-4-isothiazolin-3-one Intermediate for Example 3

To a suspension of 209 g (0.6 mol) of N,N'-bis-(n-pentyl)-3,3'-dithiodipropionamide in 600 ml of ethyl acetate at 40° C. was added 134.0 g (1.9 mol) of chlorine over a one hour period. After the addition, the resulting mixture was allowed to cool to room temperature, degassed, and evaporated under reduced pressure to give the hydrochloride salt of 2-n-pentyl-4-isothiazolin-3-one as a solid. This solid was added to a mixture of 300 ml of water and 200 ml of chloroform. Solid sodium bicarbonate was added in portions with stirring unitl the aqueous phase was at pH 7-8. The layers were separated and the aqueous phase extracted with additional chloroform. The combined chloroform extracts were dried over magnesium sulfate and evaporated to give a brown oil. Vacuum distillation of the oil gave 161 g (82% yield) of the 2-n-pentyl-4-isothiazolin-3-one intermediate, bp=118° C./0.05 mm.

C. Preparation of 2-n-Heptyl-4-isothiazolin-3-one Intermediate for Example 4

To a slurry of 75 g (0.185 mol) of N,N'-bis-(n-heptyl)-3,3'-dithiodipropionamide in 600 ml of toluene was added 39.4 g (0.555 mol) of chlorine over a one hour period at 25°-40° C. The mixture was stirred for one additional hour and cooled to room temperature. The yellow solution was washed with water and the toluene phase was dried over magnesium sulfate and concentrated. The residual oil was dissolved in ether and then saturated with HCl gas. The resulting solid precipitate was removed by filtration and dissolved in water. The aqueous solution was extracted several times with ether. The combined ether extracts were dried over magnesium sulfate and concentrated under reduced pressure to give 30.7 g (83% yield) of the 2-n-heptyl-4-isothiazolin-3-one intermediate as a heavy, colorless oil which was not distilled.

D. Preparation of 2-n-Hexyl-4-isothiazolin-3-one Intermediate for Example 5

To a mixture of 37.6 g (0.1 mol) of N,N'-bis-(n-hexyl)-3,3'dithiodipropionamide and 400 ml of ethylene dichloride at room temperature was added 42.2 g (0.315 mol) of sulfuryl chloride over a one hour period. The clear yellow solution was stirred at room temperature overnight and then concentrated. The residue was diluted with ether which was washed with sodium bicarbonate solution, dried over magnesium sulfate, and then concentrated to give a brown oil. The oil was distilled at 105°-115° C./0.04 mm to give 35 g of crude product. This distillate was dissolved in ether and treated with HCl gas to precipitate the hydrochloride salt of the 2-n-hexyl-4-isothiazolin-3-one. This salt was removed by filtration, triturated with water, and then extracted several times with ether. The combined ether extract was dried over magnesium sulfate and concentrated. The residual oil was vacuum distilled to give 28.8 g (87% yield) of pure 2-n-hexyl-4-isothiazolin-3-one intermediate as a yellow oil, bp=102° C./0.03 mm.

E. Preparation of 2-Cyclohexyl-4,5-dichloro-4-isothiazolin-3-one Intermediate for Example 6

To 400 ml of ethyl acetate at 0° C. was added simultaneously over a one hour period 148 g (0.4 mol) of N,N'-bis-(cyclohexyl)-3,3'-dithiodipropionamide, in forty 3.7 g portions at 1.5 minute intervals, and 116.5 g (1.64 mol) of chlorine. The temperature was maintained between 0°-5° C. during the addition and then the mixture was allowed to warm to 15° C. The resulting solid was collected and found to be cyclohexylamine hydrochloride. Concentration of the filtrate gave additional cyclohexylamine hydrochloride mixed with an oil. The oil was dissolved by trituration with acetone and then filtered. The filtrate was decolorized using activated charcoal and evaporated to a mush. Recrystallization of the mush from 300 ml of methanol yielded 21.6 g (11% yield) of the 2-cyclohexyl-4,5-dichloro-4-isothiazolin-3-one intermediate, mp=113.5°-115.5° C.

F. Preparation of 2-n-Hexyl-4,5-dichloro-4-isothiazolin-3-one Intermediate for Example 7

To a solution of 9.2 g (0.05 mol) of N,N'-bis-(n-hexyl)-3,3'-dithiodipropionamide in 100 ml of ethyl acetate at room temperature was added 10.65 g (0.15 mol) of chlorine over a 30 minute period. During the addition, the temperature of the mixture rose to 53° C. and slowly dropped near the end. After cooling to room temperature, the mixture was concentrated under reduced pressure. The resulting amber oil, 17.8 g, was column chromatographed on silica gel using toluene as the eluant. A by-product, 2-n-hexyl-4,4,5,5-tetrachloro-4-isothiazolin-3-one, eluted first as 4.8 g of an oil which distilled at 128°-133° C./0.3 mm.

The desired 2-n-hexyl-4,5-dichloro-4-isothiazolin-3-one intermediate eluted later from the column as 8.2 g (60% yield) of an oil which distilled at 130°-136° C./0.35 mm.

EXAMPLES 8, 9, 10, and 69

Preparation of Other Compounds of the Invention

Example 1 was also repeated with the replacement of the 2,4-pentanedione by 3,5-heptanedione, 5,5-dimethyl-1,3-cyclohexanedione, 2,4-hexanedione, and ethyl benzoylacetate, respectively, to obtain Examples 8, 9, 10, and 69 as shown in Table 1.

EXAMPLE 11

Preparation of N-n-Octyl-cis-3-[2-(ethoxy-3-oxobutanoyl)thio]acrylamide

To a dry 250 ml flask equipped with a mechanical stirrer, thermometer, and nitrogen inlet adaptor was placed 75 ml of absolute ethanol. Sodium metal (0.36 g, 0.016 mol) was added in pieces with stirring under nitrogen. When all the sodium dissolved, a solution of 2.23 g (0.017 mol) of ethyl acetoacetate in 10 ml of methylene chloride was added over a 5 minute period. After 15 minutes, a solution of 2-n-octyl-4-isothiazolin-3-one (3.0 g, 0.014 mol) in 10 ml of methylene chloride was added over a 10 minute period. The mixture was stirred for an additional 20 minutes and then cooled to 5° C. The mixture was poured into 30 ml of an ice-cold 2N HCl solution with stirring. The mixture was diluted with water and extracted with methylene chloride. The methylene chloride extract was dried over magnesium sulfate and concentrated. The residual thick, yellow oil solidified upon standing. The solid mass was triturated with a small amount of ether and removed by filtration to give 4.1 g (85% yield) of N-n-octyl-cis-3-[2-(ethoxy-3-oxobutanoyl)thio]acrylamide which had a mp of 84°-86° C.

EXAMPLE 12

Preparation of
N-n-Octyl-cis-3-2-(N-benzoylacetoacetamido)thio]acrylamide

Example 11 was repeated except for the replacement of the ethyl acetoacetate by 3.27 g (0.017 mol) of N-benzylacetoacetamide to obtain 5.2 g (62% yield) of N-n-octyl-cis-3-[2-(N-benzoylacetoacetamido)thio]acrylamide which had a mp of 91°-94° C.

EXAMPLE 18

Preparation of
N-n-Octyl-cis-3-[2-(ethyl-N-n-octylmalonamido)thio]acrylamide

To a stirred, cooled (0° C.) solution of 21.5 g (0.143 mol) of ethyl malonyl chloride in 250 mL of methylene chloride under nitrogen was added dropwise a solution of 18.47 g (0.143 mol) of n-octylamine in 100 mL of methylene chloride over a half-hour period. After the addition the reaction mixture was allowed to warm to room temperature and stir for 2 h. The reaction mixture was cooled to 0° C. and a solution of 20 mL (0.143 mol) of triethylamine in 100 mL of methylene chloride was added dropwise over 2 h. Additional methylene chloride was added to keep the slurry of salts stirring efficiently. After the addition the reaction mixture was kept cold in a freezer. After 12 h the reaction was allowed to warm to room temperature and was immediately washed with water three times to remove the salts. The organic layer was dried over magnesium sulfate and filtered. Removal of solvent gave 29.5 g (84% yield) of ethyl N-n-octylmalonamide as a pale yellow solid.

In an oven-dried 1 L flask under nitrogen was placed 2.9 g (0.12 mol) of hexane-washed sodium hydride in 250 mL of tetrahydrofuran (freshly distilled from sodium-benzophenone ketyl). To this slurry was added a solution of 30 g (0.12 mol) of ethyl N-n-octylmalonamide in 100 mL of freshly-distilled tetrahydrofuran dropwise with stirring over a half-hour period. The mixture was then stirred for an additional 1.5 h during which time it became homogeneous. The mixture was cooled to 0° C. and a solution of 25.5 g (0.12 mol) of 2-n-octyl-4-isothiazolin-3-one in 150 mL of freshly-distilled tetrahydrofuran was added dropwise with stirring. After the addition the mixture was allowed to warm to room temperature and stir for 2 h. The mixture was then poured into 10% aqueous hydrochloric acid and extracted three times with methylene chloride. The combined organic layers were washed with water until the washes were neutral in pH. The organic solution was washed with brine, dried over magnesium sulfate, and filtered. Removal of solvents afforded 54 g of a crude solid. Recrystallization from hexane/ethyl acetate gave 32.8 g (60% yield) of N-n-octyl-cis-3-[2-(ethyl-N-n-octylmalonamido)thio]acrylamide white crystalline solid, mp 110°-112° C. as shown in Table 1.

EXAMPLES 13-17, 36, 37, 43, 49-51, 60 and 62-66

The procedure of Example 18 was repeated with the replacement of n-octylamine in the first step by one of the following commercially available amines: n-butylamine, isobutylamine, n-propylamine, sec-butylamine, n-hexylamine, cyclopropylamine, 2-propenylamine, 2-cyano-4-chloroaniline, 3-(aminomethyl)pyridine, 3-chloro-4-methoxyaniline, 3-morpholinopropylamine, 4-methoxybenzylamine, 2-aminopyrimidine, 4-aminomorpholine, 4-nitrobenzylamine, 3-nitrobenzylamine, and 2-(2-aminoethyl)pyridine in order to obtain Examples 13, 14, 15, 16, 17, 36, 37, 43, 49, 50, 51, 60, 62, 63, 64, 65, and 66, respectively, as shown in Table 1.

EXAMPLE 19

Preparation of
N-n-Octyl-cis-3-[2-(N,N'-di-n-propylmalonodiamido)-thio]acrylamide To 2.28 mL (0.015 mol) of diethyl malonate under nitrogen was added 2.5 mL (0.03 mol) of n-propylamine with stirring. This mixture was allowed to stir overnight during which time the product had crystallized out of solution. The crystals were filtered and washed with ethyl acetate to give 1.2 g (43% yield) of white crystals of N,N'-di-n-propylmalonamide.

To a solution of 0.055 g (2.5 mmol) of hexane-washed sodium hydride in 15 mL of tetrahydrofuran under nitrogen was added 0.465 g (2.5 mmol) of N,N'-di-n-propylmalonamide in 15 mL of N,N-dimethylformamide and 15 mL of tetrahydrofuran. This mixture was stirred at room temperature for 1 h, and was then cooled to 0° C. A solution of 0.5 g (2.3 mmol) of 2-n-octyl-4-isothiazolin-3-one in 5 mL of tetrahydrofuran was added dropwise. The mixture was allowed to warm to room temperature and stir for 2 h. The mixture was poured into 2N aqueous hydrochloric acid, diluted with water, and extracted with ethyl acetate. The combined organic layers were dried over magnesium sulfate, filtered, and stripped of solvents to give a yellow solid. Recrystallization from 75% ethyl acetate/hexane afforded 0.27 g (30% yield) of N-n-octyl-cis-3-[2-N,N'-di-n-propylmalonodiamido)thio]acrylamide as a white solid, m.p. 152°-154° C. as shown in Table 1.

EXAMPLE 23

Preparation of
N-n-Octyl-cis-3-{2-[ethyl-N-(3-methoxyphenyl)-malonamido]thio}acrylamide To a stirred, cooled (0° C.) solution of 2.13 mL (0.017 mol) of ethyl malonyl chloride in 10 mL of methylene chloride under nitrogen was added dropwise a solution of 2.03 mL (0.017 mol) of m-anisidine in 10 mL of methylene chloride over a half-hour period. After the addition the reaction mixture was allowed to warm to room temperature and stir for 2 h. The reaction mixture was cooled to 0° C. and a solution of 2.36 mL (0.017 mol) of triethylamine in 10 mL of methylene chloride was added dropwise over 2 h. Additional methylene chloride was added to keep the slurry of salts stirring efficiently. After the addition the reaction mixture was kept cold by placing it in the freezer. After 12 h the reaction was allowed to warm to room temperature and was immediately washed with water three times to remove the salts. The organic layer was dried over magnesium sulfate and filtered. Removal of solvent gave a crude oil. Purification by flash-chromatography (silica gel, 25% ethyl acetate/hexane eluent) afforded 2.5 g (64% yield) of ethyl N-3-methoxyphenylmalonamide as a red oil.

To 10 mL of absolute ethanol under nitrogen was added 0.1 g (0.005 mol) of sodium metal with stirring. After the sodium had completely reacted a solution of 1.09 g (0.005 mol) of ethyl N-3-methoxyphenylmalonamide in 5 mL of absolute ethanol was added. After 15 min this solution was cooled to 0° C. and a solution of 1.0 g (0.005 mol) of 2-n-octyl-4-isothiazolin-3-one in 10 mL of absolute ethanol was added dropwise. After 30 min the mixture was poured into 2N aqueous hydrochloric acid, diluted with water, and extracted three times with ethyl ether. The combined organic layers were washed with brine, dried over magnesium sulfate, and filtered. Removal of solvents gave a crude solid which was triturated with 25% ethyl acetate/hexane and filtered to yield 1.01 g (52% yield) of N-n-octyl-cis-3-{2-[ethyl-N-(3-methoxyphenyl)malonamido]thio}acrylamide as a white crystalline solid, m.p. 122°-124° C., as shown in Table 1.

EXAMPLES 20-22

The procedured Example 23 was repeated with one of the following commercially available amines instead of 3-anisidine: benzylamine, 2-chloroaniline, and 4-chlorobenzylamine to give Examples 20, 21, and 22, respectively, as shown in Table 1.

EXAMPLE 29

Preparation of
N-n-Octyl-cis-3-[2-(1-cyclopropyl-1,3-butanedionyl)-thio]acrylamide To a stirred solution of 8.4 g (0.1 mol) of cyclopropyl methyl ketone in 100 mL of ethyl acetate under nitrogen was added dropwise 39 mL (0.1 mol) of a 21 wt % solution of sodium ethoxide in absolute ethanol. The flask was fitted with a condenser and Dean-Stark trap and was heated. The ethanol was removed by azeotropic distillation. Additional ethyl acetate was added to the flask as needed. After three hours the temperature of the distillate had reached 75° C. and the reaction was allowed to cool and stand overnight. The white solid which precipitated out was collected by filtration and the filtrate was set aside. The solid was dissolved in water and this solution was acidified at 0° C. with 10% aqueous hydrochloric acid. This solution was extracted three times with ethyl ether. The ethyl acetate filtrate was washed with water three times, acidified with 10% aqueous hydrochloric acid, and extracted with ethyl ether. The ether extracts from both extractions were combined, dried over magnesium sulfate, and filtered. Removal of solvents gave 3.5 g of 1-cyclopropyl-1,3-butanedione as an oil. Analysis by GC showed 75% purity. This intermediate was used without further purification.

To 25 mL of absolute ethanol under nitrogen was added 3.0 mL (0.009 mol) of 21 wt % of sodium ethoxide in absolute ethanol. To this stirred solution was added a solution of 1.63 g (0.009 mol) of the 1-cyclopropyl-1,3-butanedione intermediate in 15 mL of absolute ethanol. After 15 min this solution was cooled to 0° C. and a solution of 2.0 g (0.009 mol) of 2-n-octyl-4-isothiazolin-3-one in 10 mL of absolute ethanol was added dropwise with stirring. After the addition was complete the mixture was allowed to warm to room temperature and stir for 12 h. The mixture was poured into ice-cold 10% aqueous hydrochloric acid, diluted with water, and extracted three times with ethyl ether. The combined organic layers were washed with brine, dried over magnesium sulfate, and filtered. Removal of solvents gave a solid which was recrystallized from ethyl acetate/hexane to give 1.2 g (40% yield) of N-n-octyl-cis-3-[2-(1-cyclopropyl-1,3-butanedionyl)thio]acrylamide as a white solid, m.p. 81°-83° C., shown in Table 1.

EXAMPLE 31

Preparation of
N-n-Octyl-cis-3-[2-(N-phenylacetoacetamido)thio]acrylamide

To a stirred, cooled (0° C.) solution of 1.26 mL (0.01 mol) of diisopropylamine in 25 mL of freshly-distilled tetrahydrofuran under nitrogen was added 6.43 mL (0.01 mol) of a 1.4M solution of n-butyllithium in hexanes. After 10 min a solution of 1.66 g (0.01 mol) of acetoacetanilide in 10 mL of tetrahydrofuran was added dropwise. After 15 min a solution of 2.0 g (0.01 mol) of 2-n-octyl-4-isothiazolin-3-one in 15 mL of tetrahydrofuran was added dropwise. After this addition the reaction was allowed to warm to room temperature and stir for 2 days. The mixture was poured into ice-cold 10% aqueous hydrochloric acid, diluted with 25 mL of water, and extracted three times with ethyl acetate. The combined organic layers were washed with water, brine, and dried over magnesium sulfate. Filtration and removal of solvents gave a brown oil which was chromatographed (silica gel, ethyl acetate/hexane eluent) to give a brown solid. This solid was recrystallized from ethyl acetate/hexane to give 0.78 g (20% yield) of N-n-octyl-cis-3-[2-(N-phenylacetoacetamido)thio]acrylamide as a tan solid, m.p. 130°-133° C., and is reported in Table 1.

EXAMPLES 30, 47 and 57

The procedure of Example 31 was repeated with one of the following commercially-available amines instead of acetoacetanilide: 2-acetoacetanisidine, 4-acetoacetanisidine, and 2-acetoacetotoluidine to give Examples 30, 47, and 57, respectively, as reported in Table 1.

EXAMPLE 39

Preparation of
N-n-Octyl-cis-3-{2-[ethyl-N-(2-methyl-3-chlorophenyl)malonamido]thio}acrylamide To a stirred, cooled (0° C.) solution of 2.0 g (0.013 mol) of ethyl malonyl chloride in 15 mL of methylene chloride under nitrogen was added dropwise a solution of 1.88 g (0.013 mol) of 2-methyl-3-chloroaniline in 10 mL of methylene chloride over a half-hour period. After the addition the reaction mixture was allowed to warm to room temperature and stir for 2 h. The reaction mixture was cooled to 0° C. and a solution of 1.87 mL (0.013 mol) of triethylamine in 10 mL of methylene chloride was added dropwise over 2 h. Additional methylene chloride was added to keep the slurry of salts stirring efficiently. After the addition the reaction mixture was kept cold by placing it in the freezer. After 12 h the reaction was allowed to warm to room temperature and was immediately washed with water three times to remove the salts. The organic layer was dried over magnesium sulfate and filtered. Removal of solvent gave 3.28 g (96% yield) of ethyl N-2-methyl-3-chlorophenylmalonamide as a pale yellow solid.

To a stirred, cooled (0° C.) solution of 0.75 g (0.0075 mol) of diisopropylamine in 50 mL of freshly-distilled tetrahydrofuran under nitrogen was added 5.35 mL (0.0075 mol) of a 1.4M solution of n-butyllithium in hexanes. After 10 min a solution of 1.91 g (0.0075 mol) of ethyl N-2-methyl-3-chlorophenylmalonamide in 25 mL of tetrahydrofuran was added dropwise. After 15 min a solution of 1.6 g (0.0075 mol) of 2-n-octyl-4-isothiazolin-3-one in 25 mL of tetrahydrofuran was added dropwise. After this addition the reaction was allowed to warm to room temperature and stir for 2 days. The mixture was poured into ice-cold 10% aqueous hydrochloric acid, diluted with 25 mL of water, and extracted three times with chloroform. The combined organic layers were washed two times with water, brine, and dried over magnesium sulfate. Filtration and removal of solvents gave a brown solid. Trituration with 25% ethyl acetate/hexane and filtration gave 1.82 g (52% yield) of N-n-octyl-cis-3-{2-[ethyl-N-(2-methyl-3-chlorophenyl)-malonamido]thio}acrylamide as a white solid, m.p. 108°–110° C., as shown in Table 1.

EXAMPLES 24–28, 32–35, 38, 40, 41, 44–46, 48, 52–56, 58 and 59

The procedure of Example 39 was run with the replacement of 3-anisidine with one of the following commercially-available amines: n-dodecylamine, 2-aminothiazole, n-decylamine, 5-cyanopentylamine, 2-thiophenemethylamine, 3-methoxybenzylamine, 4-methylbenzylamine, 3-chloroaniline with one, 2,3-dichloro34 aniline, 2-chlorobenzylamine, 3-methylbenzylamine, 2,3-dichloroaniline, 2-aminopyridine, 2-chloro-5-nitroaniline, 2-methoxy-5-chloroaniline, 3-nitro-4-chloroaniline, 2,4-dichloroaniline, 2-anisidine, 3-toluidine, 3,5-dichloroaniline, 2-methoxybenzylamine, 4-anisidine, and 2-chloro-6-methylaniline to give Examples 24, 25, 26, 27, 28, 32, 33, 34, 35, 38, 40, 41, 44, 45, 46, 48, 52, 53, 54, 55, 56, 58, and 59, respectively, as listed in Table 1.

EXAMPLE 42

Preparation of
N-n-Octyl-cis-3-{2-[ethyl-N-(2-chloro-5-methylphenyl)malonamido]thio}acrylamide To a stirred, cooled (0° C.) solution of 2.0 g (0.013 mol) of ethyl malonyl chloride in 10 mL of methylene chloride under nitrogen was added dropwise a solution of 1.88 g (0.013 mol) of 2-chloro-5-methylaniline in 10 mL of methylene chloride over a half-hour period. After the addition the reaction mixture was allowed to warm to room temperature and stir for 2 h. The reaction mixture was cooled to 0° C. and a solution of 1.87 mL (0.013 mol) of triethylamine in 10 mL of methylene chloride was added dropwise over 2 h. After the addition the reaction mixture was kept cold by placing it in the freezer. After 12 h the reaction was allowed to warm to room temperature and was immediately washed with water three times to remove the salts. The organic layer was dried over magnesium sulfate and filtered. Removal of solvent gave 2.8 g (84% yield) of ethyl N-2-chloro-5-methylphenylmalonamide as a tan solid.

In an oven-dried 1 L flask under nitrogen was placed 0.12 g (0.005 mol) of hexane-washed sodium hydride in 15 mL of tetrahydrofuran (freshly distilled from sodium-benzophenone ketyl). To this slurry was added a solution of 1.28 g (0.005 mol) of said ethyl N-2-chloro-5-methylphenylmalonamide in 10 mL of freshly-distilled tetrahydrofuran dropwise with stirring over a half-hour period. The mixture was then stirred for an additional 1.5 h during which time it became homogeneous. The mixture was cooled to 0° C. and a solution of 1.06 g (0.005 mol) of 2-n-octyl-4-isothiazolin-3-one in 10 mL of freshly-distilled tetrahydrofuran was added dropwise with stirring. After the addition the mixture was allowed to warm to room temperature and stir for 2.5 h. The mixture was then poured into 10% aqueous hydrochloric acid and extracted three times with methylene chloride. The combined organic layers were washed with water until the washes were neutral in pH. The organic solution was washed with brine, dried over magnesium sulfate, and filtered. Removal of solvents afforded a crude oil. Purification by chromatography (silica gel, ethyl acetate/hexane eluent) gave 0.3 g (13% yield) of N-n-octyl-cis-3-{2-[ethyl-N-(2-chloro -5-methylphenyl)malonamido]thio}acrylamide as a pale yellow solid, mp 114° C. This structure is shown in Table 1.

EXAMPLE 61

Preparation of
N-n-Octyl-cis-3-[2-(N-benzyl-N'-n-octyl-malonodiamido)thio]acrylamide To a stirred, cooled (0° C.) solution of 14 g (0.093 mol) of ethyl malonyl chloride in 50 mL of methylene chloride under nitrogen was added dropwise a solution of 10 g (0.093 mol) of benzylamine in 50 mL of methylene chloride over a half-hour period. After the addition the reaction mixture was allowed to warm to room temperature and stir for 2 h. The reaction mixture was cooled to 0° C. and a solution of 13 mL (0.093 mol) of triethylamine in 50 mL of methylene chloride was added dropwise over 2 h. Additional methylene chloride was added to keep the slurry of salts stirring efficiently. After the addition the reaction mixture was kept cold by placing it in the freezer. After 12 h the reaction was allowed to warm to room temperature and was immediately washed with water three times to remove the salts. The organic layer was dried over magnesium sulfate and filtered. Removal of solvent gave a crude product which was purified by flash-chromatography (silica gel, 50% ethyl acetate/hexane eluent) to give 12.5 g (61% yield) of ethyl N-benzylmalonamide.

A solution of 1.1 g (5.0 mol) of ethyl N-benzylmalonamide in 30 mL of toluene was heated to reflux under nitrogen and 1.29 g (10.0 mol) of n-octylamine was added. The reaction was heated to reflux for 5 h and 5 mL of N,N-dimethylformamide was added. This mixture was kept at reflux for 12 h and poured into 5% aqueous hydrochloric acid. the organic layer was washed with saturated aqueous sodium bicarbonate, water, brine, and dried over magnesium sulfate. Filtration and removal of solvents afforded a crude solid which was recrystallized from 50% ethyl acetate/hexane to give 0.8 g (53% yield) of N-n-octyl-N'-benzyl-malonamide.

In an oven-dried 1 L flask under nitrogen was placed 0.071 g (2.8 mmol) of hexane-washed sodium hydride in 10 mL of tetrahydrofuran (freshly distilled from sodium-benzophenone ketyl). To this slurry was added a solution of 0.8 g (2.6 mmol) of N-n-octyl-N'-benzyl-malonamide in 10 mL of freshly-distilled tetrahydrofuran dropwise with stirring over a half-hour period. The mixture was then stirred for an additional 1.5 h at 0° C. followed by gentle warming for 1 h. The mixture was cooled to 0° C. and a solution of 0.55 g (2.6 mmol) of 2-n-octyl-4-isothiazolin-3-one in 10 mL of freshly-distilled tetrahydrofuran was added dropwise with stirring. After the addition the mixture was allowed to warm to room temperature and stir for 2 h. The mixture was then poured into 10% aqueous hydrochloric acid and extracted three times with methylene chloride. The combined organic layers were washed with water until the washes were neutral in pH. The organic solution was washed with brine, dried over magnesium sulfate, and filtered. Removal of solvents afforded a crude solid. Recrystallization from ethyl acetate/hexane afforded 0.36 g (27% yield) of N-n-octyl-cis-3-[2-(N-benzy-N'-n-octylmalonodiamido)thio]acrylamide as a white crystalline solid, mp 131°-135° C. This is reported in Table 1.

EXAMPLE 67

Preparation of
N-n-Octyl-cis-3-[2-(1,3-diphenyl-1,3-propanedionyl)thio]acrylamide To a stirred solution of 2.25 g (0.01 mol) of 1,3-diphenyl-1,3-propanedione in 25 mL of N,N-dimethylformamide under nitrogen was added dropwise 10 mL (0.01 mol) of a 1M solution of tetrabutylammonium fluoride in tetrahydrofuran. After 15 min a solution of 2.13 g (0.01 mol) of 2-n-octyl-4-isothiazolin-3-one in 5 mL of N,N-dimethylformamide was added. The reaction was allowed to stir for one week and was poured into 10% aqueous hydrochloric acid. This mixture was extracted three times with ethyl acetate. The combined organic layers were washed with brine, dried over magnesium sulfate, and filtered. Removal of solvents gave a crude solid which was purified by flash-chromatography (silica gel, ethyl acetate/hexane eluent) to give 0.1 g of N-n-octyl-cis-3-[2-1,3-diphenyl-1,3-propanedionyl)thio]acrylamide as a white solid, m.p. 137°-139° C. See Table 1.

EXAMPLE 68

Preparation of
N-n-Octyl-cis-3-{2-[1-phenyl-3-(1-methylpyrrol-2-yl)-1,3-propanedionyl]thio}acrylamide To a stirred, cooled (5° C.) slurry of 0.96 g (0.04 mol) of hexane-washed sodium hydride in 2.72 g (0.02 mol) of methyl benzoate under nitrogen was added a solution of 5.0 g (0.04 mol) of 2-acetyl-1-methylpyrrole in 30 mL of ethyl ether. A few drops of ethanol were added. The reaction mixture was allowed to stir at 5° C. for 12 h. The mixture was poured into water and extracted with ethyl ether. The combined organic layers were washed with brine, dried over magnesium sulfate, and filtered. Removal of solvents gave a waxy solid which was purified by flash-chromatography (silica gel, ethyl acetate/hexane as eluent) to give 0.8 g of 1-(1-methylpyrrol-2-yl)-3-phenyl-1,3-propanedione.

To a stirred solution of 0.78 g (0.0034 mol) of 1-(1-methylpyrrol-2-yl)-3-phenyl-1,3-propanedione in 5 mL of N,N-dimethylformamide under nitrogen was added 3.4 mL (0.0034 mol) of a 1M solution of tetrabutylammonium fluoride in tetrahydrofuran. After 10 min a solution of 0.73 g (0.0034 mol) of 2-n-octyl-4-isothiazolin-3-one in 5 mL of N,N-dimethylformamide was added. After 12 h another 3.4 mL of the 1M tetrabutylammonium fluoride solution was added. After 12 h the reaction mixture was diluted with 10% aqueous hydrochloric acid and extracted three times with ethyl acetate. The combined organic layers were washed several times with water, once with brine, and dried over magnesium sulfate. Removal of solvents and recrystallization of the crude product from ethyl acetate/hexane gave 0.28 g (19% yield) of N-n-Octyl-cis-3-{[1-phenyl-3-(1-methylpyrrol-2-yl)-1,3-propanedionyl]thio}acrylamide as a white solid, m.p. 131°-132° C. See Table 1.

TABLE 1

| | | Structure of Compounds Related to Formula I | | | | |
|---|---|---|---|---|---|---|
| Example | Melting Point (°C.) | $R_1$ | $Z_2$ | $Z_1$ | $R_2$ | $R_3$ |
| 1 | 87–89 | —(CH$_2$)$_7$CH$_3$ | —H | —H | —CH$_3$ | —CH$_3$ |
| 2 | 34–36 | —(CH$_2$)$_7$CH$_3$ | —Cl | —Cl | —CH$_3$ | —CH$_3$ |
| 3 | 123–125 | —(CH$_2$)$_4$CH$_3$ | —H | —H | —CH$_3$ | —CH$_3$ |
| 4 | 86–87 | —(CH$_2$)$_6$CH$_3$ | —H | —H | —CH$_3$ | —CH$_3$ |
| 5 | 91–94 | —(CH$_2$)$_5$CH$_3$ | —H | —H | —CH$_3$ | —CH$_3$ |
| 6 | 162–164 | (cyclohexyl) | —Cl | —Cl | —CH$_3$ | —CH$_3$ |
| 7 | oil | —(CH$_2$)$_5$CH$_3$ | —Cl | —Cl | —CH$_3$ | —CH$_3$ |
| 8 | 195–199 | —(CH$_2$)$_7$CH$_3$ | —H | —H | —C$_2$H$_5$ | —C$_2$H$_5$ |
| 9 | 147–152 | —(CH$_2$)$_7$CH$_3$ | —H | —H | —CH$_2$C(CH$_3$)$_2$CH$_2$— | ($R_2 + R_3$ taken together) |
| 10 | 77–81 | —(CH$_2$)$_7$CH$_3$ | —H | —H | —C$_2$H$_5$ | —CH$_3$ |
| 11 | 84–86 | —(CH$_2$)$_7$CH$_3$ | —H | —H | —CH$_3$ | —OC$_2$H$_5$ |
| 12 | 91–94 | —(CH$_2$)$_7$CH$_3$ | —H | —H | —CH$_3$ | —NHCH$_2$φ |
| 13 | 97–98 | —(CH$_2$)$_7$CH$_3$ | —H | —H | —OC$_2$H$_5$ | —NH(CH$_2$)$_3$CH$_3$ |
| 14 | 106–112 | —(CH$_2$)$_7$CH$_3$ | —H | —H | —OC$_2$H$_5$ | —NHCH$_2$CH(CH$_3$)$_2$ |
| 15 | 100–102 | —(CH$_2$)$_7$CH$_3$ | —H | —H | —OC$_2$H$_5$ | —NH(CH$_2$)$_2$CH$_3$ |
| 16 | 146–147 | —(CH$_2$)$_7$CH$_3$ | —H | —H | —OC$_2$H$_5$ | —NHCH(CH$_3$)CH$_2$CH$_3$ |
| 17 | 110–111 | —(CH$_2$)$_7$CH$_3$ | —H | —H | —OC$_2$H$_5$ | —NH(CH$_2$)$_5$CH$_3$ |
| 18 | 110–112 | —(CH$_2$)$_7$CH$_3$ | —H | —H | —OC$_2$H$_5$ | —NH(CH$_2$)$_7$CH$_3$ |
| 19 | 152–154 | —(CH$_2$)$_7$CH$_3$ | —H | —H | —NHCH$_2$CH$_2$CH$_3$ | —NHCH$_2$CH$_2$CH$_3$ |

TABLE 1-continued

| Example | Melting Point (°C.) | R₁ | Z₂ | Z₁ | R₂ | R₃ |
|---|---|---|---|---|---|---|
| 20 | (nmr data)* | —(CH₂)₇CH₃ | —H | —H | —OC₂H₅ | —NHCH₂φ |
| 21 | (nmr data)* | —(CH₂)₇CH₃ | —H | —H | —OC₂H₅ | —NH—(2-chlorophenyl) |
| 22 | 145–148 | —(CH₂)₇CH₃ | —H | —H | —OC₂H₅ | —NHCH₂—(4-chlorophenyl) |
| 23 | 122–124 | —(CH₂)₇CH₃ | —H | —H | —OC₂H₅ | —NH—(3-methoxyphenyl) |
| 24 | 106–108 | —(CH₂)₇CH₃ | —H | —H | —OC₂H₅ | —NH(CH₂)₁₁CH₃ |
| 25 | 158–160 | —(CH₂)₇CH₃ | —H | —H | —OC₂H₅ | —NH—(thiazol-2-yl) |
| 26 | 105–106.5 | —(CH₂)₇CH₃ | —H | —H | —OC₂H₅ | —NH(CH₂)₉CH₃ |
| 27 | 98–100 | —(CH₂)₇CH₃ | —H | —H | —OC₂H₅ | —NH(CH₂)₅CN |
| 28 | 117–119 | —(CH₂)₇CH₃ | —H | —H | —OC₂H₅ | —NH—(thien-2-yl) |
| 29 | 81–83 | —(CH₂)₇CH₃ | —H | —H | —CH₃ | (cyclopropyl) |
| 30 | 99–102 | —(CH₂)₇CH₃ | —H | —H | —CH₃ | —NH—(2-methoxyphenyl) |
| 31 | 130–133 | —(CH₂)₇CH₃ | —H | —H | —CH₃ | —NHφ |
| 32 | 114–115 | —(CH₂)₇CH₃ | —H | —H | —OC₂H₅ | —NHCH₂—(3-methoxyphenyl) |
| 33 | 125–126 | —(CH₂)₇CH₃ | —H | —H | —OC₂H₅ | —NHCH₂—(4-methylphenyl) |
| 34 | 130–133 | —(CH₂)₇CH₃ | —H | —H | —OC₂H₅ | —NH—(4-chlorophenyl) |

TABLE 1-continued

Structure of Compounds Related to Formula 1

| Example | Melting Point (°C.) | $R_1$ | $Z_2$ | $Z_1$ | $R_2$ | $R_3$ |
|---|---|---|---|---|---|---|
| 35 | 94-96 | $-(CH_2)_7CH_3$ | $-H$ | $-H$ | $-OC_2H_5$ | $-NH-$(2,3-dichlorophenyl) |
| 36 | 128-131 | $-(CH_2)_7CH_3$ | $-H$ | $-H$ | $-OC_2H_5$ | $-NH-$cyclopropyl |
| 37 | 109-112 | $-(CH_2)_7CH_3$ | $-H$ | $-H$ | $-OC_2H_5$ | $-NHCH_2CH=CH_2$ |
| 38 | 138-140 | $-(CH_2)_7CH_3$ | $-H$ | $-H$ | $-OC_2H_5$ | $-NHCH_2-$(2-chlorophenyl) |
| 39 | 108-110 | $-(CH_2)_7CH_3$ | $-H$ | $-H$ | $-OC_2H_5$ | $-NH-$(2-methyl-3-chlorophenyl) |
| 40 | 127-129 | $-(CH_2)_7CH_3$ | $-H$ | $-H$ | $-OC_2H_5$ | $-NHCH_2-$(3-methylphenyl) |
| 41 | (nmr data)* | $-(CH_2)_7CH_3$ | $-H$ | $-H$ | $-OC_2H_5$ | $-NH-$(2,4-dichlorophenyl) |
| 42 | 114 | $-(CH_2)_7CH_3$ | $-H$ | $-H$ | $-OC_2H_5$ | $-NH-$(2-chloro-5-methylphenyl) |
| 43 | (nmr data)* | $-(CH_2)_7CH_3$ | $-H$ | $-H$ | $-OC_2H_5$ | $-NH-$(4-chloro-2-cyanophenyl) |
| 44 | 154-155 | $-(CH_2)_7CH_3$ | $-H$ | $-H$ | $-OC_2H_5$ | $-NH-$(2-pyridyl) |
| 45 | 117-119 | $-(CH_2)_7CH_3$ | $-H$ | $-H$ | $-OC_2H_5$ | $-NH-$(2-nitro-5-chlorophenyl) |

TABLE 1-continued

| Example | Melting Point (°C.) | R$_1$ | Z$_2$ | Z$_1$ | R$_2$ | R$_3$ |
|---|---|---|---|---|---|---|
| 46 | 118-120 | —(CH$_2$)$_7$CH$_3$ | —H | —H | —OC$_2$H$_5$ | —NH-(5-Cl, 2-OCH$_3$-phenyl) |
| 47 | (nmr data)* | —(CH$_2$)$_7$CH$_3$ | —H | —H | —CH$_3$ | —NH-(4-OCH$_3$-phenyl) |
| 48 | (nmr data)* | —(CH$_2$)$_7$CH$_3$ | —H | —H | —OC$_2$H$_5$ | —NH-(2-NO$_2$, 4-Cl-phenyl) |
| 49 | (nmr data)* | —(CH$_2$)$_7$CH$_3$ | —H | —H | —OC$_2$H$_5$ | —NHCH$_2$-(3-pyridyl) |
| 50 | 129-131 | —(CH$_2$)$_7$CH$_3$ | —H | —H | —OC$_2$H$_5$ | —NH-(3-Cl, 4-OCH$_3$-phenyl) |
| 51 | 89-93 | —(CH$_2$)$_7$CH$_3$ | —H | —H | —OC$_2$H$_5$ | —NH(CH$_2$)$_3$N(morpholino) |
| 52 | 127-133 | —(CH$_2$)$_7$CH$_3$ | —H | —H | —OC$_2$H$_5$ | —NH-(3,4-diCl-phenyl) |
| 53 | 105-108 | —(CH$_2$)$_7$CH$_3$ | —H | —H | —OC$_2$H$_5$ | —NH-(2-OCH$_3$-phenyl) |
| 54 | 105-107 | —(CH$_2$)$_7$CH$_3$ | —H | —H | —OC$_2$H$_5$ | —NH-(3-CH$_3$-phenyl) |
| 55 | 118-122 | —(CH$_2$)$_7$CH$_3$ | —H | —H | —OC$_2$H$_5$ | —NH-(3,5-diCl-phenyl) |
| 56 | 98-100 | —(CH$_2$)$_7$CH$_3$ | —H | —H | —OC$_2$H$_5$ | —NHCH$_2$-(2-OCH$_3$-phenyl) |

TABLE 1-continued

| Example | Melting Point (°C.) | Structure of Compounds Related to Formula I | | | | $R_3$ |
|---|---|---|---|---|---|---|
| | | $R_1$ | $Z_2$ | $Z_1$ | $R_2$ | |
| 57 | 88-104 | —(CH$_2$)$_7$CH$_3$ | —H | —H | —CH$_3$ | —NH—(2-methylphenyl) |
| 58 | 139-141 | —(CH$_2$)$_7$CH$_3$ | —H | —H | —OC$_2$H$_5$ | —NH—(4-methoxyphenyl) |
| 59 | 152-154 | —(CH$_2$)$_7$CH$_3$ | —H | —H | —OC$_2$H$_5$ | —NH—(2-chloro-6-methylphenyl) |
| 60 | 102-105 | —(CH$_2$)$_7$CH$_3$ | —H | —H | —OC$_2$H$_5$ | —NHCH$_2$—(4-methoxyphenyl) |
| 61 | 131-135 | —(CH$_2$)$_7$CH$_3$ | —H | —H | —(CH$_2$)$_7$CH$_3$ | —NHCH$_2$—phenyl |
| 62 | 163-165 (dec) | —(CH$_2$)$_7$CH$_3$ | —H | —H | —OC$_2$H$_5$ | —NH—(pyrimidin-2-yl) |
| 63 | 116-121 | —(CH$_2$)$_7$CH$_3$ | —H | —H | —OC$_2$H$_5$ | —NH—N(morpholino) |
| 64 | 148-151 | —(CH$_2$)$_7$CH$_3$ | —H | —H | —OC$_2$H$_5$ | —NHCH$_2$—(4-nitrophenyl) |
| 65 | 136-138 | —(CH$_2$)$_7$CH$_3$ | —H | —H | —OC$_2$H$_5$ | —NHCH$_2$—(3-nitrophenyl) |
| 66 | (nmr data)* | —(CH$_2$)$_7$CH$_3$ | —H | —H | —OC$_2$H$_5$ | —NHCH$_2$CH$_2$—(pyridin-2-yl) |
| 67 | 137-139 | —(CH$_2$)$_7$CH$_3$ | —H | —H | -φ | -φ |
| 68 | 130-132 | —(CH$_2$)$_7$CH$_3$ | —H | —H | -φ | —(1-methylpyrrol-2-yl) |
| 69 | 100-105 | —(CH$_2$)$_7$CH$_3$ | —H | —H | —OC$_2$H$_5$ | -φ |

TABLE 2

NMR Data for Certain Examples

| Example | NMR Data |
|---|---|
| 20 | $^1$H-NMR 60MHz(CDCl$_3$, Me$_4$Si)δ0.8(brt, CH$_2$—CH$_3$), 1.0–1.6(m), 1.3(t, J=8Hz, O—CH$_2$—CH$_3$), 3.25(m, NH—CH$_2$—), 4.25(s, S—CH), 4.3(q, OCH$_2$—CH$_3$), 5.95(d, J=10Hz, C=CH—CO), 7.1(d, J=10Hz, C=CH—S), 7.2(m, aromatic H), 8.2(brs, NH), 8.35 ppm(d, J=3Hz, NH). |
| 21 | $^1$H-NMR 60MHz(CDCl$_3$, d$^6$-acetone, d$^6$-DMSO, Me$_4$Si)δ 0.8(brt, CH$_2$CH$_3$), 1.0–1.6(m), 1.3(t, J=8Hz, OCH$_2$CH$_3$), 3.25(m, NH—CH$_2$), 3.75(s, OCH$_3$), 4.2(q, OCH$_2$CH$_3$), 4.55(s, S—CH), 6.0(d, J=10Hz, C=CH—CO), 7.1(d, J=10Hz, C=CH—S), 7.2(m, aromatic H), 8.4 ppm(m, NH). |
| 41 | $^1$H-NMR 60MHz(CDCl$_3$, Me$_4$Si)δ0.8(brt, CH$_2$CH$_3$), 1.0–1.6(m), 1.3(t, J=8Hz, OCH$_2$CH$_3$), 3.25(m, NH—CH$_2$), 4.15(s, S—CH), 4.2(q, OCH$_2$CH$_3$), 5.95(d, J=10Hz, C=CH—CO), 7.0(d, J=10Hz, C=CH—S), 7.2(m, aromatic H), 8.0(m, aromatic H), 9.0 ppm(s, NH). |
| 43 | $^1$H-NMR 60MHz(CDCl$_3$, Me$_4$Si)δ0.8(brt, CH$_2$CH$_3$), 1.0–1.6(m), 1.3(t, 8Hz, OCH$_2$CH$_3$), 3.3(m, NH—CH$_2$), 4.35(s, S—CH), 4.35(q, OCH$_2$CH$_3$), 6.05(d, J=10Hz, C=CH—CO), 7.1(d, J=10Hz, C=CH—S), 7.6(m, aromatic H), 8.2(d, J=10Hz, NH), 9.7 ppm(brs, NH). |
| 47 | $^1$H-NMR 60MHz(CDCl$_3$, Me$_4$Si)δ0.8(brt, CH$_2$CH$_3$), 1.0–1.6(m), 2.25(s, COCH$_3$), 3.3(m, NH—CH$_2$), 3.7(s, OCH$_3$), 5.8–7.4(m, aromatic H & CH=CH), 8.4 ppm(brs, NH). |
| 48 | $^1$H-NMR 60MHz(CDCl$_3$, Me$_4$Si)δ0.8(brt, CH$_2$CH$_3$), 1.0–1.6(m), 1.3(t, J=8Hz, OCH$_2$CH$_3$), 3.3(m, NH—CH$_2$), 4.2(q, OCH$_2$CH$_3$), 4.5(s, S—CH), 5.9(d, J=10Hz, C=CH—CO), 7.0–7.6(m, aromatic H and C=CH—S), 8.2 ppm(m, NH). |
| 49 | $^1$H-NMR 60MHz(CDCl$_3$, Me$_4$Si)δ0.8(brt, CH$_2$CH$_3$), 1.0–1.6(m), 1.3(t, J=8Hz, OCH$_2$CH$_3$), 3.2(m, NH—CH$_2$), 4.1(q, OCH$_2$CH$_3$), 4.3(s, S—CH), 4.4(m, CH$_2$-pyr), 5.9(d, J=10Hz, C=CH—CO), 6.5(m), 7.0(d, J=10Hz, C=CH—S), 7.0–8.0(m), 8.4 ppm(m). |
| 66 | $^1$H-NMR 200MHz(CDCl$_3$, Me$_4$Si)δ0.85(t, J=6Hz, CH$_2$—CH$_3$), [1.1–1.4(m), 1.25(t, J=8Hz, OCH$_2$CH$_3$)], 1.4–1.6(m, NH—CH$_2$—CH$_2$), 3.0(m, —NH—CH$_2$—CH$_2$-pyr), 3.7(dq, NH—CH$_2$), 4.15(s, S—CH), 4.2(q, OCH$_2$—CH$_3$), 5.8(d, J=9Hz, C=CHCO), 7.05(d, J=9Hz, C=CH—S), 7.1(m), 8.5 ppm(m, NH). |

EX. NO. NAME

1. N-n-octyl-cis-3-[3-(2,4-pentanedionyl)thio]acrylamide
2. N-n-octyl-2,3-dichloro-cis-3-[3-(2,4-pentanedionyl)thio]acrylamide
3. N-n-pentyl-cis-3-[3-(2,4-pentanedionyl)thio]acrylamide
4. N-n-heptyl-cis-3-[3-(2,4-pentanedionyl)thio]acrylamide
5. N-n-hexyl-cis-3-[3-(2,4-pentanedionyl)thio]acrylamide
6. N-cyclohexyl-2,3-dichloro-cis-3-[3-(2,4-pentanedionyl)thio]acrylamide
7. N-n-hexyl-2,3-dichloro-cis-3-[3-(2,4-pentanedionyl)thio]acrylamide
8. N-n-octyl-cis-3-[4-(3,5-heptanedionyl)thio]acrylamide
9. N-n-octyl-cis-3-[2-(5,5-dimethyl-1,3-cyclohexanedionyl)thio]acrylamide
10. N-n-octyl-cis-3-[3-(2,4-hexanedionyl)thio]acrylamide
11. N-n-octyl-cis-3-[2-(ethoxy-3-oxobutanoyl)thio]acrylamide
12. N-n-octyl-cis-3-[2-(N-benzylacetoacetamideo)thio]acrylamide
13. N-n-octyl-cis-3-[2-(ethyl-N-n-butylmalonamido)thio]acrylamide
14. N-n-octyl-cis-3-[2-(ethyl-N-(2-methylpropyl)-malonamido)thio]acrylamide
15. N-n-octyl-cis-3-[2-(ethyl-N-n-propylmalonamido)-thio]acrylamide
16. N-n-octyl-cis-3-[2-(ethyl-N-(1-methylpropyl)-malonamido)thio]acrylamide
17. N-n-octyl-cis-3-[2-(ethyl-N-n-hexylmalonamido)thio]acrylamide
18. N-n-octyl-cis-3-[2-(ethyl-N-n-octylmalonamido)thio]acrylamide
19. N-n-octyl-cis-3-[2-(N,N'-di-n-propyl-malonodiamido)thio]acrylamide
20. N-n-octyl-cis-3-[2-(ethyl-N-benzylmalonamido)thio]acrylamide
21. N-n-octyl-cis-3-{2-[ethyl-N-(2-chlorophenyl)-malonamido]thio}acrylamide
22. N-n-octyl-cis-3-{2-[ethyl-N-(4-chlorobenzyl)-malonamido]thio}acrylamide
23. N-n-octyl-cis-3-{2-[ethyl-N-(3-methoxyphenyl)-malonamido]thio}acrylamide
24. N-n-octyl-cis-3-[2-(ethyl-N-n-dodecylmalonamido)-thio]acrylamide
25. N-n-octyl-cis-3-{2-[ethyl-N-(2-thiazoyl)-malonamido]thio}acrylamide
26. N-n-octyl-cis-3-[2-(ethyl-N-n-decylmalonamido)thio]acrylamide
27. N-n-octyl-cis-3-{2-[ethyl-N-(5-cyanopentyl)-malonamido]thio}acrylamide
28. N-n-octyl-cis-3-{2-[ethyl-N-(2-thiophenylmethyl)-malonamido]thio}acrylamide
29. N-n-octyl-cis-3-[2-(1-cyclopropyl-1,3-butanedionyl)-thio]acrylamide
30. N-n-octyl-cis-3-{2-[N-(2-methoxyphenyl)acetoacetamido]thio}acrylamide
31. N-n-octyl-cis-3-[2-(N-phenylacetoacetamido)thio]acrylamide
32. N-n-octyl-cis-3-{2-[ethyl-N-(3-methoxybenzyl)-malonamido]thio}acrylamide
33. N-n-octyl-cis-3-{2-[ethyl-N-(4-methylbenzyl)-malonamido]thio}acrylamide
34. N-n-octyl-cis-3-{2-[ethyl-N-(4-chlorophenyl)-malonamido]thio}acrylamide
35. N-n-octyl-cis-3-{2-[ethyl-N-(2,3-dichlorophenyl)-malonamido]thio}acrylamide
36. N-n-octyl-cis-3-[2-(ethyl-N-cyclopropyl-malonamido)thio]acrylamide
37. N-n-octyl-cis-3-{2-[ethyl-N-(2-propenyl)-malonamido]thio}acrylamide
38. N-n-octyl-cis-3-[2-(ethyl-N-(2-chlorobenzyl)-malonamido)thio]acrylamide
39. N-n-octyl-cis-3-{2-[ethyl-N-(2-methyl-3-chlorophenyl)malonamido]thio}acrylamide
40. N-n-octyl-cis-3-{2-[ethyl-N-(3-methylbenzyl)-malonamido]thio}acrylamide
41. N-n-octyl-cis-3-{2-[ethyl-N-(2,4-dichlorophenyl)-malonamido]thio}acrylamide
42. N-n-octyl-cis-3-{2-[ethyl-N-(2-chloro-5-methylphenyl)malonamido]thio}acrylamide
43. N-n-octyl-cis-3-{2-[ethyl-N-(2-cyano-4-chlorophenyl)malonamido]thio}acrylamide
44. N-n-octyl-cis-3-{2-[ethyl-N-(2-pyridyl)-malonamido]thio}acrylamide
45. N-n-octyl-cis-3-{2-[ethyl-N-(2-chloro-5-nitrophenyl)malonamido]thio}acrylamide
46. N-n-octyl-cis-3-{2-[ethyl-N-(2-methoxy-5-chlorophenyl)malonamido]thio}acrylamide
47. N-n-octyl-cis-3-{2-[N-(4-methoxyphenyl)acetoacetamido]thio}acrylamide
48. N-n-octyl-cis-3-{2-[ethyl-N-(3-nitro-4-chlorophenyl)malonamido]thio}acrylamide 49  N-n-octyl-cis-3-{2-[ethyl-N-((3-pyridyl)methyl)-malonamido]thio}acrylamide
50  N-n-octyl-cis-3-{2-[ethyl-N-(3-chloro-4-methoxyphenyl)malonamido]thio}acrylamide
51  N-n-octyl-cis-3-{2-[ethyl-N-(3-(4-morpholino)propyl)malonamido]thio}acrylamide
52  N-n-octyl-cis-3-{2-[ethyl-N-(3,4-dichlorophenyl)-malonamido]thio}acrylamide
53  N-n-octyl-cis-3-{2-[ethyl-N-(2-methoxyphenyl)-malonamido]thio}acrylamide
54  N-n-octyl-cis-3-{2-[ethyl-N-(3-methylphenyl)-malonamido]thio}acrylamide
55  N-n-octyl-cis-3-{2-[ethyl-N-(3,5-dichlorophenyl)-malonamido]thio}acrylamide
56  N-n-octyl-cis-3-{2-[ethyl-N-(2-methoxybenzyl)-malonamido]thio}acrylamide
57  N-n-octyl-cis-3-{2-[N-(2-methylphenyl)acetoacetamido]thio}acrylamide
58  N-n-octyl-cis-3-{2-[ethyl-N-(4-methoxyphenyl)-malonamido]thio}acrylamide
59  N-n-octyl-cis-3-{2-[ethyl-N-(2-chloro-6-methylphenyl)malonamido]thio}acrylamide
60  N-n-octyl-cis-3-{2-[ethyl-N-(4-methoxybenzyl)-malonamido]thio}acrylamide
61  N-n-octyl-cis-3-[2-(N-benzyl-N'-n-octyl-malonodiamido)thio]acrylamide
62  N-n-octyl-cis-3-{2-[ethyl-N-(2-pyrimidinyl)-malonamido]thio}acrylamide
63  N-n-octyl-cis-3-{2-[ethyl-N-(4-morpholino)-malonamido]thio}acrylamide
64  N-n-octyl-cis-3-{2-[ethyl-N-(4-nitrobenzyl)-malonamido]thio}acrylamide
65  N-n-octyl-cis-3-{2-[ethyl-N-(3-nitrobenzyl)-malonamido]thio}acrylamide
66  N-n-octyl-cis-3-{2-[ethyl-N-(2-(2-pyridyl)ethyl)-malonamido]thio}acrylamide
67  N-n-octyl-cis-3-[2-(1,3-diphenyl-1,3-propanedionyl)-thio]acrylamide
68  N-n-octyl-cis-3-{2-[1-phenyl-3-(1-methylpyrroyl-2-yl)-1,3-propanedionyl]thio}acrylamide
69  N-n-octyl-cis-3-[2-(ethoxy-3-phenyl-3-oxopropanoyl)thio]acrylamide

EXAMPLE 70

Biocidal Activity

The compounds of Examples 1, 2, 6, 18, 42, 49 and 49 were tested using the following procedures, with the results reported in Table 3.

The Speed of Kill (SOK) Test measures the loss of cell viability in an aqueous suspension of bacterial cells during a four hour period when these cells are contacted with a defined concentration of the test compound in synthetic hard water (SHW). A stock solution or dispersion of the test compound, typically at a concentration of 1%, is made in a 5:3:2 solvent solution of acetone, methanol, and water. The SHW is made by taking one liter of sterile deionized water and adding the following solutions to it:

1. 2 ml of a solution of 31.74 g of $MgCl_2$ and 73.99 g of $CaCl_2$ in 1000 ml of sterile distilled water which has been heat sterillized.
2. 4 ml of a solution of 56.03 g of $NaHCO_3$ in 1000 ml of water which has been filter sterillized.

The combined solution is then filter sterilized to yield the SHW. A volume of the stock solution is dispensed into the SHW to give an initial test compound starting concentration of 500 ppm.

When the test is ready to be run, each vessel in the dilution series, except the first vessel, contains an equal volume of the SHW mixture with the test compound. The first vessel contains twice the volume of SHW with the starting concentration of test compound. One half of the SHW from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm, respectively.

Each vessel is then inoculated with a cell suspension of the ps.fl bacteria. The bacteria were grown on a 1% agar slant tube and incubated for 18-24 hours at 30° C. Thereafter, the tube is washed with four ml of sterile water. This was is diluted to a density of 60 to 80 Nephlolmeter Turbidity Units (NTU). To 100 ml of the SHW containing the various concentrations of the test compound is added 0.75 ml of inoculum from the 60-80 NTU wash with good mixing. After 4 hours from the time of addition at 30° C., 5 μl of solution is transferred to 100 μl of a broth solution in order to recover any living cells. This mixture is incubated for 24 hours at 30° C. before noting the concentration in ppm at which each compound killed >99.999% of the cells in the SHW solution.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm, respectively.

Each vessel is then inoculated with a cell suspension of the appropriate test organism. Bacteria are grown in broth and fungi on agar slants for a time and at a temperature appropriate to the species being tested. At the end of the growth period, the broth is vortexed to disperse the cells. In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound. The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity include:

BACTERIA

*Pseudomonas fluorescens* (Ps.fl), gram negative
*Pseudomonas aerugenosa* (Ps.ae), gram negative

*Escherichia coli* (E.c), gram negative
*Staphylococcus aureus* (S.a), gram positive

FUNGI

*Aspergillus niger* (A.n)
*Aureobasidium pullulans* (A.p)

TABLE 3

| | SOK and MIC Test Results in Ppm | | | | | | |
|---|---|---|---|---|---|---|---|
| Compound of Ex. | SOK | Ps.fl | Ps.ae | E.c | S.a | A.n | A.p |
| 1 | >500 | >500 | <4 | >500 | <4 | 8 | <4 |
| 2 | >500 | >500 | <4 | >500 | <4 | 8 | <4 |
| 6 | >500 | >500 | 32 | 500 | 16 | 125 | <4 |
| 18 | 16 | <4 | >500 | 250 | 8 | <4 | <4 |
| 42 | 125 | 8 | >500 | 500 | 8 | <4 | 16 |
| 49 | >500 | >500 | <4 | >500 | <4 | <4 | <4 |
| 69 | >500 | >500 | 32 | 500 | 16 | 125 | <4 |

The compounds of Examples 1–68 were subjected also to the following alternate biocidal activity test procedures, with the results as indicated in Table 4.

Speed of Kill Test

The SOK test measures the viability of Pseudomonas fluorescens inoculum in synthetic hard water (SHW) when exposed for 24 hours to a 100 ppm acetone solution of a given compound.

An acetone solution of the compound was prepared at 10,000 ppm and 0.1 ml was added to 9.8 ml of SHW. 0.1 ml of Ps fl inoculum at 10,000,000 cells per ml was added to the SHW, providing 10 ml of solution which was incubated for 24 hours prior to recovery into Tryptic Soy Broth (TSB).

To recover and measure the living cells, 2.5 ml of the SHW mix was transferred to a reservoir from which 2.5 μl was then transferred 8 times to microtiter wells containing 225 μl of TSB. Each of the 8 transfers was then serially diluted seven times, providing eight replicates of eight dilutions. The concentration at which no living cells were recovered was used to back calculate the log reduction. The data was entered into the database, and the log reductions calculated automatically.

Minimum Inhibitory Concentration Test

The MIC test measures the viability of Pseudomonas fluorescens inoculum in TSB when exposed for 72 hours to varying concentrations of test compound.

A 125 μl aliquot of 10,000 ppm test compound in acetone was added to 4.88 ml of TSB to provide a 250 ppm solution. From this solution, 100 μL was transferred to the first row of two microtiter plate columns. Both replicates and five additional compounds were all serially diluted 1:1 to a final concentration of 0.8 ppm in TSB.

Inoculation was accomplished by diluting a 24 hr Ps fl culture, four mls per 36 mls of phosphate buffer solution. A Dynatech autoinoculator was used to transfer 1.5 μl of this cell suspension to the microtiter plates. The plates were incubated at 30° C. for 3 days before the lowest concentration at which no growth occurs was recorded in the database. The SOK data and MIC test data on Ps.fl, Ps.ae, E.c, and S.a. bacteria and Candida albicans (C.alb), A.n and A.p fungi are listed in Table 4.

TABLE 4

| | SOK and MIC Test Results in Ppm | | | | | | | |
|---|---|---|---|---|---|---|---|---|
| Compound of Ex. | SOK | A.n | A.p | C.alb | E.c | Ps.ae | Ps.fl | S.a |
| 1 | >100 | >500 | * | * | * | * | >500 | * |
| 2 | >100 | >500 | * | * | * | * | >500 | * |
| 3 | >100 | 31–63 | 8 | 31 | 125–250 | >500 | >500 | 125 |
| 4 | >100 | 16–63 | <4 | <4 | >500 | >500 | >500 | 63 |
| 5 | >100 | 31–63 | <4 | 16 | >500 | >500 | >500 | 63–125 |
| 6 | <100 | >500 | * | * | * | * | >500 | * |
| 7 | >100 | 8–63 | 8 | 31 | 125 | 500 | 250–500 | 125 |
| 8 | >100 | >500 | * | * | * | * | >500 | * |
| 9 | >100 | >500 | * | * | * | * | >500 | * |
| 10 | >100 | >500 | * | * | * | * | >500 | * |
| 11 | >100 | 4–8 | <4 | <4 | >500 | >500 | 250–500 | >500 |
| 12 | >100 | 4–16 | 8 | 16 | >500 | >500 | 125–500 | >500 |
| 13 | * | * | * | * | * | * | * | * |
| 14 | * | * | * | * | * | * | * | * |
| 15 | >100 | 63 | * | * | * | * | >500 | * |
| 16 | >100 | >500 | * | * | * | * | >500 | * |
| 17 | >100 | >500 | * | * | * | * | >500 | * |
| 18 | >100 | >500 | * | * | * | * | >500 | * |
| 19 | >100 | >500 | * | * | * | * | >500 | * |
| 20 | >100 | >500 | * | * | * | * | >500 | * |
| 21 | >100 | 8 | * | * | * | * | >500 | * |
| 22 | >100 | >500 | * | * | * | * | >500 | * |
| 23 | >100 | >500 | * | * | * | * | >500 | * |
| 24 | >100 | 250 | * | * | * | * | >500 | * |
| 25 | >100 | >500 | * | * | * | * | >500 | * |
| 26 | >100 | >500 | * | * | * | * | >500 | * |
| 27 | >100 | >500 | * | * | * | * | >500 | * |
| 28 | >100 | 16–31 | ** | 63 | 500 | 500 | 500 | 500 |
| 29 | >100 | 8–31 | 125 | 31 | >500 | >500 | >500 | >500 |
| 30 | >100 | 31–63 | 250 | 8 | >500 | 500 | >500 | >500 |
| 31 | >100 | 250 | * | * | * | * | 500 | * |
| 32 | >100 | 500 | * | * | * | * | >500 | * |
| 33 | >100 | 250–500 | * | * | * | * | >500 | * |
| 34 | >100 | >500 | * | * | * | * | >500 | * |
| 35 | >100 | 8–16 | <2 | 4 | >250 | >250 | 500 | >250 |
| 36 | >100 | 8–16 | <2 | 31 | >250 | >250 | 500 | 125 |
| 37 | >100 | 4–8 | <2 | 8 | >250 | >250 | 500 | 31 |
| 38 | >100 | 125–250 | * | * | * | * | >500 | * |

TABLE 4-continued

| Compound of Ex. | SOK | SOK and MIC Test Results in Ppm | | | | | | |
|---|---|---|---|---|---|---|---|---|
| | | A.n | A.p | C.alb | E.c | Ps.ae | Ps.fl | S.a |
| 39 | >100 | 500 | * | * | * | * | >500 | * |
| 40 | >100 | 125-250 | * | * | * | * | >500 | * |
| 41 | >100 | 8-31 | 8 | 63 | >500 | >500 | >500 | >500 |
| 42 | * | * | * | * | * | * | * | * |
| 43 | * | * | * | * | * | * | * | * |
| 44 | >100 | 250 | * | * | * | * | >500 | * |
| 45 | >100 | 4-8 | <2 | 4 | >250 | >250 | >250 | 63 |
| 46 | >100 | 250 | * | * | * | * | >500 | * |
| 47 | >100 | 4-16 | <2 | 4 | >250 | >250 | >250 | 31 |
| 48 | >100 | 4-31 | <2 | 31 | >250 | >250 | >250 | >250 |
| 49 | * | * | * | * | * | * | * | * |
| 50 | >100 | ** | <2 | 63-250 | >250 | >250 | >250 | >250 |
| 51 | >100 | <2 | <2 | <2 | >250 | >250 | >250 | 31 |
| 52 | >100 | >500 | * | * | * | * | >500 | * |
| 53 | >100 | 500 | * | * | * | * | >500 | * |
| 54 | >100 | >500 | * | * | * | * | >500 | * |
| 55 | >100 | >500 | * | * | * | * | >500 | * |
| 56 | >100 | 250 | * | * | * | * | >500 | * |
| 57 | >100 | 250 | * | * | * | * | >500 | * |
| 58 | >100 | 250 | * | * | * | * | >500 | * |
| 59 | >100 | 250 | * | * | * | * | >250 | * |
| 60 | >100 | >250 | * | * | * | * | >250 | * |
| 61 | >100 | >250 | * | * | * | * | >250 | * |
| 62 | >100 | >250 | * | * | * | * | >250 | * |
| 63 | >100 | 2-16 | <2 | <2 | 250 | >250 | >250 | 31 |
| 64 | >100 | >250 | * | * | * | * | >250 | * |
| 65 | >100 | >250 | * | * | * | * | >250 | * |
| 66 | >100 | <2 | <2 | <2 | >250 | >250 | >250 | 63 |
| 67 | * | * | * | * | * | * | * | * |
| 68 | >100 | * | * | * | * | * | >250 | * |

*Test was not run.
**Test did not replicate.

EXAMPLE 71

The compounds of Examples 1-68 were tested for fungicial activity according to the following test procedures with the results as reported in Table 5.

The compounds of this invention were tested for fungicidal activity in vivo against cucumber downy mildew (CDM), rice blast (RB), rice sheath blight (RSB), tomato late blight (TLB), wheat powdery mildew (WPM), wheat stem rust (WSR) and wheat leaf rust (WLR). In tests on cereals (except for rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water, acetone, and methanol, sprayed onto the plants, allowed to dry (four to six hours), and then the plants were inoculated with the fungus. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

Cucumber Downy Mildew (CDM)

*Pseudoperonospora cubensis* was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° F. to 75° F. Seven days after inoculation, the percent disease control was determined.

Rice Blast (RB)

Nato rice plants were inoculated with *Piricularia oryzae* (about 20,000 conidia per ml) by spraying the leaves and stems with an airbrush until a uniform film of inoculum was observed on the leaves. The inoculate plants were incubated in a humid environment (75° F. to 85° F.) for about 24 hours, then placed in a greenhouse environment (70° F. to 75° F.). Seven to eight days after inoculation, the percent disease control was determined.

Rice Sheath Blight (RSB)

*Pellicularia filamentosa* (f. sp. sasiki) was cultured on an autoclaved mixture of crushed rice seeds and potato dextrose broth (100 gms of rice seeds per 30 ml of potato dextrose broth) in a 500 ml Erlenmeyer flask. After 10 days, the culture was blended in a blender to produce a uniform inoculum. Approximately one teaspoon of inoculum was spread among Lebonnet rice seedlings on the soil surface of each pot (3 inch diameter). The inoculated seedlings were incubated for 5 days in a humidity cabinet (85° F. to 90° F.). Percent disease controls were determined immediately after removing the seedlings from the cabinet.

Tomato Late Blight (TLB)

*Phytophthora infestans* was cultured on four week old Pixie tomato plants in a controlled environment room (65° F. to 70° F. and 100% relative humidity). After storage, the spores were washed from the leaves with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room as above and scored after three more days incubation. Disease control levels were recorded as percent control four days after inoculation and five days after spraying the compounds.

Wheat Powdery Mildew (WPM)

*Erysiphe graminis* (f. sp. tritici) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

Wheat Stem Rust (WSR)

*Puccinia graminis* (f. sp. tritici Race 15B-2) was cultured on Wanzer wheat seedlings for a period of 14 days in a greenhouse. A water suspension of the spores from infested plants was obtained and the spore concentration was adjusted to about 200,000 spores per ml of deionized water. Wanzer wheat plants which had been previously treated with the fungicide compounds were inoculated by applying the stem rust spore suspension, until runoff, with a DeVilbiss atomizer at 5 lbs. per square inch air pressure. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of two weeks at which time the percent disease control was determined.

Wheat Leaf Rust (WLR)

*Puccinia recondita* (f. sp. tritici Races PKB and PLD) was cultured on seven day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultra-low freezer. When stored, spores must be heat shocked for two minutes at 40° F. before use. A spore suspension is prepared from dry uredia by adding 20 mg (9.5 million) per ml of Soltrol oil. The suspension is dispensed into gelatin capsules (0.7 ml capacity) which attach to the oil atomizers. One capsule is used per flat of twenty of the two inch square pots of seven day old Fielder wheat. After waiting for at least 15 minutes for the oil to evaporate from the wheat leaves, the plants are placed in a dark mist chamber (18°–20° C. and 100% relative humidity) for 24 hours. The plants are then put in the greenhouse for the latent period and scored after 10 days for disease levels. Protective and curative tests were inoculated one day after and two days, respectively, before spraying the plants with the test chemicals.

TABLE 5

| Compound of Ex. | CONTROL* OF FUNGUS | | | | | | |
|---|---|---|---|---|---|---|---|
| | CDM | RB | RSB | TLB | WPM | WSR | WLR |
| 1 | 100/200 | 98/200 | ** | 100/200 | 25/300 | 50/100 | —/— |
| 2 | 85/300 | 0/300 | 0/300 | 10/300 | 78/300 | 85/150 | —/— |
| 3 | 98/300 | 0/300 | 0/300 | 40/100 | 0/100 | 60/300 | —/— |
| 4 | 98/200 | 60/200 | 0/30 | 100/200 | 0/100 | 80/300 | —/— |
| 5 | 100/200 | 90/200 | 0/300 | 95/200 | 0/300 | 70/300 | —/— |
| 6 | 85/200 | 70/200 | 0/200 | 0/300 | 0/300 | 0/300 | —/— |
| 7 | 95/300 | —/— | 0/300 | 20/300 | 0/300 | 60/300 | —/— |
| 8 | 95/200 | 95/200 | 0/200 | 92/200 | 0/200 | 60/200 | —/— |
| 9 | 99/200 | 50/200 | 0/200 | 70/200 | 0/200 | 60/200 | —/— |
| 10 | 100/200 | 95/200 | 0/200 | 98/200 | 30/200 | 80/200 | —/— |
| 11 | 85/200 | 0/200 | 0/200 | 0/200 | 50/200 | —/— | 50/200 |
| 12 | 100/100 | 75/200 | 25/200 | 100/100 | 75/200 | —/— | 75/200 |
| 13 | 99/200 | 50/200 | 0/200 | 80/200 | 75/200 | —/— | 50/200 |
| 14 | 95/200 | 0/200 | 0/200 | 50/200 | 75/200 | —/— | 50/200 |
| 15 | 100/200 | 40/200 | 25/5200 | 89/200 | 25/200 | —/— | 62/200 |
| 16 | 42/200 | 40/200 | 0/200 | 47/200 | 0/200 | —/— | 72/200 |
| 17 | 100/200 | 0/200 | 0/200 | 90/200 | 0/200 | —/— | 75/200 |
| 18 | 97/200 | 25/200 | 90/300 | 92/200 | 0/200 | —/— | 74/200 |
| 19 | 95/200 | 0/200 | 0/200 | 89/200 | 25/200 | —/— | 62/200 |
| 20 | 100/200 | 90/200 | 0/200 | 90/200 | 0/200 | —/— | 75/200 |
| 21 | 97/200 | 100/200 | 0/200 | 97/200 | 62/200 | —/— | 75/200 |
| 22 | 100/200 | 90/200 | 0/200 | 99/100 | 37/200 | —/— | 50/200 |
| 23 | 92/200 | 50/200 | 0/200 | 100/200 | 47/200 | —/— | 50/200 |
| 24 | 100/200 | 0/200 | 0/200 | 50/200 | 0/200 | —/— | 50/200 |
| 25 | 100/200 | 0/200 | 50/200 | 80/200 | 0/200 | —/— | 75/200 |
| 26 | 100/200 | 50/200 | 0/200 | 80/200 | 50/200 | —/— | 75/200 |
| 27 | 100/200 | 98/200 | 0/200 | 100/200 | 0/200 | —/— | ** |
| 28 | 96/200 | 25/200 | 0/200 | 50/200 | 0/200 | —/— | ** |
| 29 | 95/200 | 77/200 | 0/200 | 85/200 | 0/200 | —/— | 0/200 |
| 30 | 100/200 | 90/200 | 0/200 | 80/200 | 0/200 | —/— | 0/200 |
| 31 | 100/200 | 95/200 | 0/200 | 95/200 | 0/200 | —/— | 50/200 |
| 32 | 99/200 | 95/200 | 0/200 | 100/200 | 0/200 | —/— | 75/200 |
| 33 | 99/200 | 90/200 | 0/200 | 95/200 | 0/200 | —/— | 0/200 |
| 34 | 85/100 | 0/100 | 0/100 | 50/100 | 50/100 | —/— | 50/100 |
| 35 | 99/100 | 0/100 | 0/100 | 95/100 | 0/100 | —/— | 50/100 |
| 36 | 100/100 | 90/100 | 0/100 | 47/100 | 0/100 | —/— | 50/100 |

TABLE 5-continued

| Compound of Ex. | CDM | CONTROL* OF FUNGUS | | | | | |
| --- | --- | --- | --- | --- | --- | --- | --- |
| | | RB | RSB | TLB | WPM | WSR | WLR |
| 37 | 100/100 | 95/100 | 0/100 | 95/100 | 50/100 | —/— | 75/100 |
| 38 | 99/100 | 50/100 | 0/100 | 95/100 | 0/100 | —/— | 0/100 |
| 39 | 100/100 | 50/100 | 0/100 | 100/100 | 50/100 | —/— | 75/100 |
| 40 | 99/100 | 50/100 | 0/100 | 100/100 | 0/100 | —/— | 75/100 |
| 41 | 100/100 | 99/100 | 0/100 | 87/100 | 50/100 | —/— | 0/100 |
| 42 | —/— | —/— | —/— | 91/100 | —/— | —/— | —/— |
| 43 | 100/100 | 100/100 | 0/100 | 80/100 | 50/100 | —/— | 75/100 |
| 44 | —/— | 50/100 | 0/100 | 0/100 | 0/100 | —/— | 75/100 |
| 45 | —/— | 0/100 | 0/100 | 0/100 | 0/100 | —/— | 50/25 |
| 46 | —/— | 80/100 | 50/100 | 0/100 | 0/100 | —/— | 50/100 |
| 47 | 100/100 | 0/100 | 0/100 | 80/100 | 0/100 | —/— | 0/100 |
| 48 | 99/100 | 0/100 | 0/100 | 99/100 | 0/100 | —/— | 50/100 |
| 49 | 85/100 | 0/100 | 0/100 | 90/100 | 50/100 | —/— | 0/100 |
| 50 | 85/100 | 0/100 | 0/100 | 0/100 | 0/100 | —/— | 50/100 |
| 51 | 99/100 | 0/100 | 0/100 | 0/100 | 0/100 | —/— | 0/100 |
| 52 | 99/100 | 80/100 | 0/100 | 80/100 | 0/100 | —/— | 0/100 |
| 53 | 100/100 | 90/100 | 0/100 | 97/100 | 0/100 | 0/100 | 0/100 |
| 54 | 97/100 | 87/100 | 0/100 | 80/100 | 0/100 | 0/100 | 0/100 |
| 55 | 85/100 | 95/100 | 0/100 | 80/100 | 50/100 | —/— | 0/100 |
| 56 | 100/100 | 90/100 | 0/100 | 80/100 | 0/100 | —/— | 0/100 |
| 57 | 0/100 | 80/100 | 100/100 | 0/100 | 50/100 | —/— | 0/100 |
| 58 | 100/100 | 0/100 | 0/100 | 0/100 | 0/100 | —/— | 0/100 |
| 59 | 99/100 | 50/100 | 0/100 | 95/100 | 0/100 | —/— | 50/100 |
| 60 | 99/100 | 0/100 | 0/100 | 80/100 | 0/100 | —/— | 0/100 |
| 61 | 99/100 | 0/100 | 0/100 | 0/100 | 0/100 | —/— | 0/100 |
| 62 | 85/100 | 0/100 | 0/100 | 0/100 | 0/100 | —/— | 0/100 |
| 63 | 99/100 | 0/100 | 0/100 | 0/100 | 0/100 | —/— | 0/100 |
| 64 | 100/100 | 0/100 | 0/100 | 0/100 | 50/100 | —/— | 50/100 |
| 65 | 100/100 | 0/100 | 0/100 | 80/100 | 0/100 | —/— | 50/100 |
| 66 | 100/100 | 0/100 | 0/100 | 40/100 | 0/100 | —/— | 0/100 |
| 67 | —/— | 90/100 | 0/100 | 0/100 | 0/100 | 0/100 | 0/100 |
| 68 | —/— | 80/100 | 0/100 | 60/100 | 0/100 | 0/100 | 0/100 |

*Values Given as % Control/Ppm Application Rate
**Test did not replicate
—/—Test not run While the invention has been described in sufficient detail for those skilled in the art to be able to make and use it, various alternatives, modifications, and improvements should become apparent from the forgoing disclosure without departing from the spirit and scope of the invention.

We claim:

1. A compound of the formula

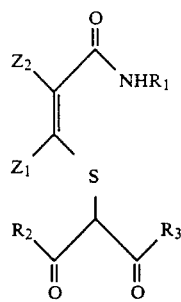

wherein
$R_1$ is $(C_5-C_{10})$alkyl or $(C_5-C_7)$cycloalkyl;
$R_2$ and $R_3$ are independently selected from the group consisting of amino, alkylamino, arylamino, aralkylamino, alkarylamino, heterocyclic substituted-amino selected from the group consisting of thiazolyl, thienyl, pyridyl, primidinyl, and pyrrolyl and alkylamino, N-containing heterocyclic aryl selected from the group consisting of 2-thiazolyl, 2-thienyl, 2-pyridyl, 3-pyridyl, 2-pyrimidinyl, 1-morpholinyl, and N-methyl-2-pyrrolyl; carbocyclic ring formed by $R_2$ and $R_3$ together; and combinations of $R_2$ and $R_3$ selected from the group consisting of —$CH_3$ and —$OC_2H_5$
—$CH_3$ and —$NHCH_2\phi$
$OC_2H_5$ and —$NH(CH_2)_3CH_3$
—$OC_2H_5$ and —$NHCH_2CH(CH_3)_2$
$OC_2H_5$ and —$NH(CH_2)_2CH_3$
$OC_2H_5$ and —$NHCH(CH_3)CH_2CH_3$
—$OC_2H_5$ and —$NH(CH_2)_5CH_3$
—$OC_2H_5$ and —$NH(CH_2)_7CH_3$
$NHCH_2CH_2CH_3$ and —$NHCH_2CH_2CH_3$
—$OC_2H_5$ and —$NHCH_2\phi$

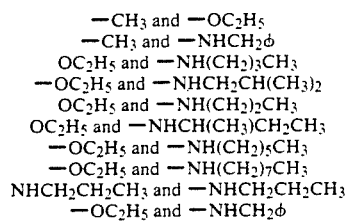

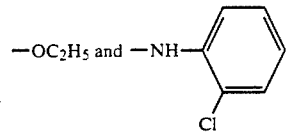

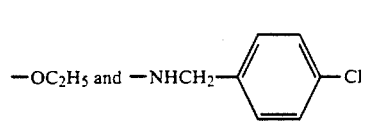

—$OC_2H_5$ and —$NH(CH_2)_{11}CH_3$

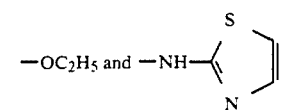

-continued
—OC₂H₅ and —NH(CH₂)₉CH₃
—OC₂H₅ and —NH(CH₂)₅CN
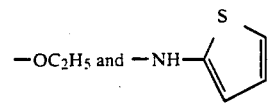
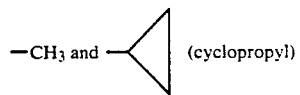
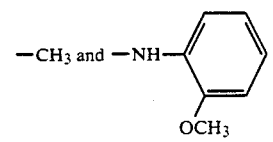
—CH₃ and —NHφ
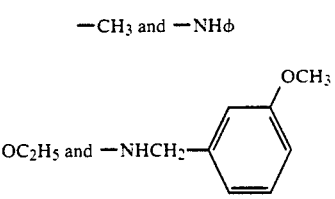
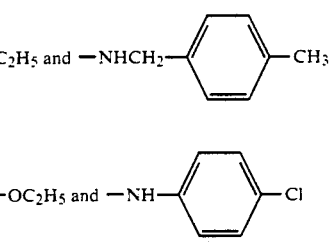
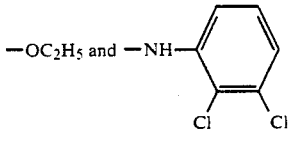
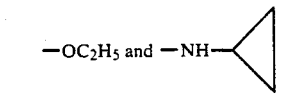
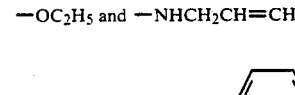
—OC₂H₅ and —NHCH₂CH=CH₂
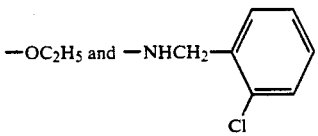
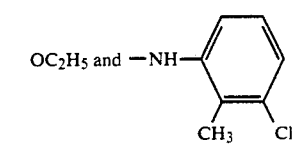
-continued
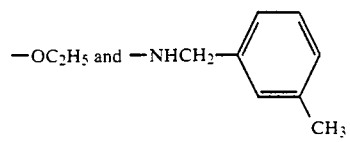
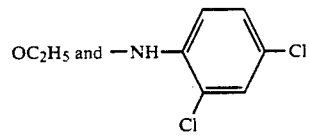
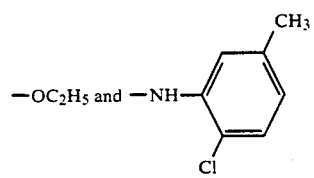
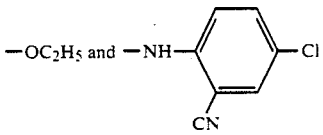
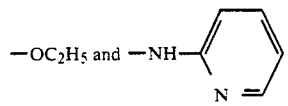
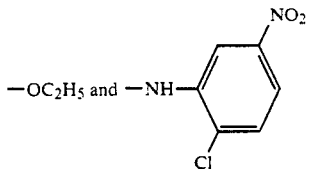
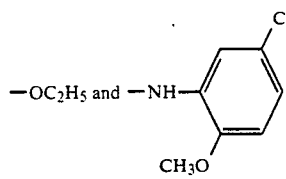
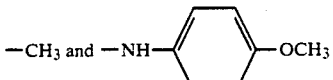
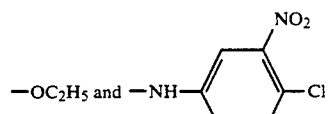
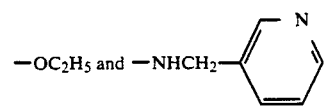
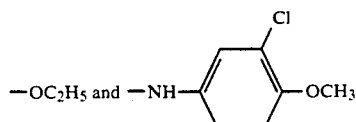

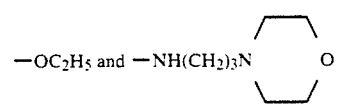
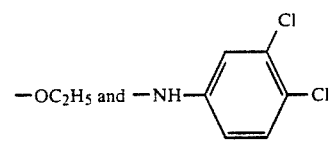
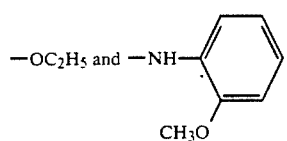
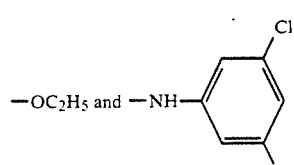
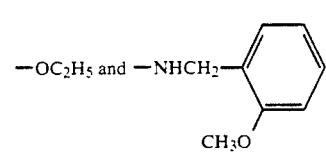
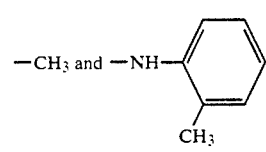
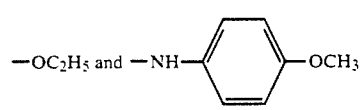
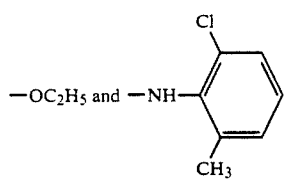
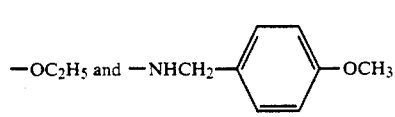
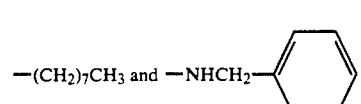
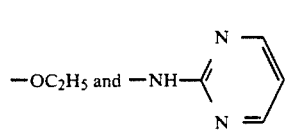

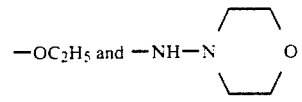
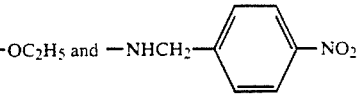
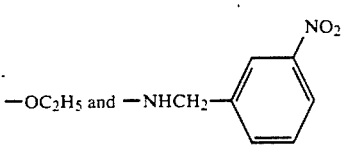
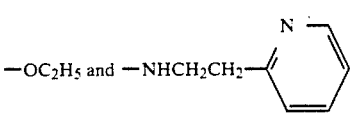
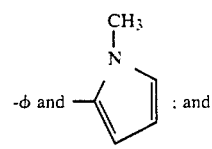

-φ and -φ

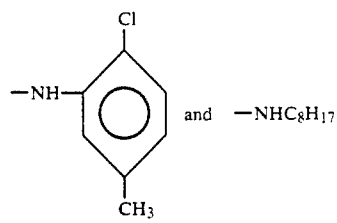

-φ and — ; and $Z_1$ and $Z_2$ are independently selected from hydrogen, halogen and $(C_1-C_4)$alkyl.

2. Compound of claim 1 wherein $R_2$ is EtO— and $R_3$ is selected from

—NH—[structure with Cl and CH3 on ring] and —NHC$_8$H$_{17}$

3. Compound of claim 1 wherein $Z_1$ and $Z_2$ are H or Cl.
4. Compound of claim 2 wherein $Z_1$ and $Z_2$ are H.
5. Compound of claim 1 wherein $R_1$ is -n-C$_8$H$_{17}$.
6. Compound of claim 2 wherein $R_1$ is -n-C$_8$H$_{17}$.
7. Compound of claim 3 wherein $R_1$ is -n-C$_8$H$_{17}$.
8. Compound of claim 4 wherein $R_1$ is -n-C$_8$H$_{17}$.
9. Method of controlling bacteria consisting of applying at, onto, or into a locus subject to contamination by said bacteria a compound according to claim 1.
10. A method for controlling a phytopathogenic fungus comprising applying to the fungus or its habitat a funicidally-effective amount of a compound of claim 1.
11. A composition comprising a compound of claim 1 in a fungicidally-effective amount and an agronomically acceptable carrier.
12. Composition comprising a compound in accordance with claim 1 and an isothiazolin-3-one of the formula

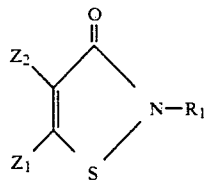

13. Method of controlling or inhibiting growth of bacteria in a locus comprising incorporating into or onto the locus a biocidally effective amount of the compound of claim 1.

14. Method of claim 13 wherein said locus is selected from the group consisting of disinfectants, sanitizers, cleaners, deodorizers, liquid and powder soaps, skin removers, oil and grease removers, food processing chemicals, dairy chemicals, food preservatives, animal food preservatives, wood preservation, paint, lazures, stains, mildewcides, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, jet fuel, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes, electrodeposition systems, diagnostic products, medical devices, water purification systems, filtration systems, fishnets and marine antifoulants.

* * * * *